United States Patent
Hanes et al.

(10) Patent No.: US 10,195,212 B2
(45) Date of Patent: Feb. 5, 2019

(54) GLUCOCORTICOID-LOADED NANOPARTICLES FOR PREVENTION OF CORNEAL ALLOGRAFT REJECTION AND NEOVASCULARIZATION

(71) Applicant: The Johns Hopkins University, Baltimore, MD (US)

(72) Inventors: Justin Scot Hanes, Baltimore, MD (US); Qing Pan, Hangzhou (CN); Qingguo Xu, Baltimore, MD (US); Nicholas J. Boylan, East Boston, MD (US); Walter J. Stark, Baltimore, MD (US); Bing Wang, Fujian Province (CN); Lixia Luo, Guangdong Province (CN)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/502,732

(22) PCT Filed: Aug. 3, 2015

(86) PCT No.: PCT/US2015/043478
§ 371 (c)(1),
(2) Date: Feb. 8, 2017

(87) PCT Pub. No.: WO2016/025215
PCT Pub. Date: Feb. 18, 2016

(65) Prior Publication Data
US 2017/0157147 A1 Jun. 8, 2017

Related U.S. Application Data

(60) Provisional application No. 62/037,000, filed on Aug. 13, 2014, provisional application No. 62/139,561, filed on Mar. 27, 2015.

(51) Int. Cl.
*A61K 31/573* (2006.01)
*A61K 9/00* (2006.01)
(Continued)

(52) U.S. Cl.
CPC .......... *A61K 31/573* (2013.01); *A61K 9/0048* (2013.01); *A61K 9/0051* (2013.01);
(Continued)

(58) Field of Classification Search
None
See application file for complete search history.

(56) References Cited

U.S. PATENT DOCUMENTS 4,432,964 A * 2/1984 Shell .................... A61K 9/0048
424/427
4,757,128 A 7/1988 Domb
(Continued)

FOREIGN PATENT DOCUMENTS

WO 2005099717 10/2005
WO 2011041373 4/2011
(Continued)

OTHER PUBLICATIONS

Jaraswekin et al. (Effect of poly(lactide-co-glycolide) molecular weight on the release of dexamethasone sodium phosphate from microparticles, Journal of Microencapsulation, 24:2, 117-128).*
(Continued)

*Primary Examiner* — Robert A Wax
*Assistant Examiner* — Melissa S Mercier
(74) *Attorney, Agent, or Firm* — Pabst Patent Group LLP

(57) ABSTRACT

Particles encapsulating a glucocorticoid such as dexamethasone sodium phosphate (DSP) into a matrix such as biodegradable poly(lactic-coglycolic acid) (PLGA) which is densely coated with hydrophilic polymer such as PEG or PLURONIC® F127, exhibit sustained release of DSP for up
(Continued)

in-vitro drug release profile (B) of DSP/PLGA nanoparticles to 7 days in vitro. These nanoparticles can be used to prevent corneal graft rejection or corneal neovascularization.

18 Claims, 17 Drawing Sheets

Specification includes a Sequence Listing.

(51) Int. Cl.
  *A61K 31/00*   (2006.01)
  *A61K 9/50*   (2006.01)
  *A61K 9/51*   (2006.01)
(52) U.S. Cl.
  CPC .......... *A61K 9/5031* (2013.01); *A61K 9/5153* (2013.01); *A61K 31/00* (2013.01)

(56) References Cited

U.S. PATENT DOCUMENTS

| | | |
|---|---|---|
| 4,789,724 A | 12/1988 | Domb |
| 4,857,311 A | 8/1989 | Domb |
| 4,888,176 A | 12/1989 | Langer |
| 5,932,462 A | 8/1999 | Harris |
| 2009/0148527 A1 | 6/2009 | Robinson |
| 2011/0206773 A1 | 8/2011 | Lavik |

FOREIGN PATENT DOCUMENTS

| | | | |
|---|---|---|---|
| WO | 2013038195 | 3/2013 | |
| WO | 2013110028 | 7/2013 | |
| WO | 2013166436 | 11/2013 | |
| WO | WO-2013166436 A1 * | 11/2013 | ........... A61K 9/5015 |

OTHER PUBLICATIONS

Aldrich et al. (Ophthalmic Preparations, Aug. 28, 2013).*
Peracchia et al. (PEG-coated Nano spheres from amphiphilic diblock and multiblock copolymers: Investigation of their drug encapsulation and release characteristics, Journal of Controlled Release, vol. 46, Issue 3, Jun. 2, 1997, pp. 223-231).*
Al-Swailem, "Graft failure: II. Ocular surface complications", Int. Ophthalmol., 28:175-189 (2008).
Amrite, et al., "Single periocular injection of celecoxib-PLGA microparticles inhibits diabetes-induced elevations in retinal PGE2, VEGF, and vascular leakage", Invest. Ophthalmol. Visual Sci., 47:1149-60 (2006).
Amrite, et al., "Size-dependent disposition of nanoparticles and microparticles following subconjunctival administration", J. Pharm. Pharmacol., 57:1555-63 (2005).
Augustin, et al., "Treatment of neovascular age-related macular degeneration: Current therapies", Clin. Ophthalmol., 3:175-82 (2009).
Ayalasomayajula, et al., "Retinal delivery of celecoxib is several-fold higher following subconjunctival administration compared to systemic administration", Pharm. Res., 21:1797-1804 (2004).
Ayalasomayajula, et al., "Subconjunctivally administered celecoxib-PLGA microparticles sustain retinal drug levels and alleviate diabetes-induced oxidative stress in a rat model", Eur. J. Pharmacol., 511:191-8 (2005).
Barnes, "Mechanisms and resistance in glucocorticoid control of inflammation", J. Steroid Biochem. Mol. Biol., 120:76-85 (2010).
Bodker, et al., "Intraocular dexamethasone penetration via subconjunctival or retrobulbar injections in rabbits", Ophthalmic Surg., 24:453-7 (1993) Abstract Only.
Cho, "Flt23k nanoparticles offer additive benefit in graft survival and anti-angiogenic effects when combined with triamcinolone", Invest. Ophthalmol. Visual Sci., 53:2328-36 (2012).
Chong and Dana, "Graft failure IV. Immunologic mechanisms of corneal transplant rejection", Int. Ophthalmol., 28:209-22 (2008).
Dana, et al., "Twenty-five-year panorama of corneal immunology—Emerging concepts in the immunopathogenesis of microbial keratitis, peripheral ulcerative keratitis, and corneal transplant rejection", Cornea, 19:625-43 (2000).
Di Tommaso, et al., "Novel micelle carriers for cyclosporin A topical ocular delivery: In vivo cornea penetration, ocular distribution and efficacy studies", Eur. J. Pharm. Biopharm., 81:257-264 (2012).
Edelhauser, et al., "Ophthalmic Drug Delivery Systems for the Treatment of Retinal Diseases: Basic Research to Clinical Applications", Invest. Ophthalmol. Visual Sci., 51:5403-20 (2010).
Ensign, et al., "Mucus-penetrating nanoparticles for vaginal drug delivery protect against herpes simplex virus", Sci. Transl. Med., 4:138ra179 (2012).
Gaudana, et al., "Recent perspectives in ocular drug delivery", Pharm. Res., 26:1197-216 (2009).
Ghate, et al., "Pharmacokinetics of intraocular drug delivery by periocular injections using ocular fluorophotometry", Invest. Ophthalmol Visual Sci., 48:2230-7 (2007).
Gomez-Graete, et al., "Encapsulation of dexamethasone into biodegradable polymeric nanoparticles", Int. J. Pharm., 331:153-9 (2007).
Gonzalez, et al., "Nanotechnology in corneal neovascularization therapy—a review", J. Ocul. Pharmacol. Ther., 29:124-34 (2013).
Hill, "Immunosuppression in corneal transplantation", Eye, 9:247-53 (1995).
Hosseini, et al., "Pharmacokinetic study of dexamethasone disodium phosphate using intravitreal, subconjunctival, and intravenous delivery routes in rabbits", J. Ocular Pharmacol. Ther., 24:301-8 (2008).
Ishihara, et al., "Efficient encapsulation of a water-soluble corticosteroid in biodegradable nanoparticles", Int. J. Pharm., 365:200-5 (2009).
Ishihara, et al., "Role of zinc in formulation of PLGA/PLA nanoparticles encapsulating betamethasone phosphate and its release profile", J. Control Release, 105:68-76 (2005).
Ishihara, et al, "Polymer Nanoparticles encapsulating betamethasone phosphate with different release profiles and stealthiness", Int J Pharm., 375:148-54 (2009b).
Ito, et al., "Update on glucocorticoid action and resistance", J. Allergy Clin. Immunol., 117:522-43 (2006).
Jiang, et al., "Intravitreal injections of GDNF-loaded biodegradable microspheres are neuroprotective in a rat model of glaucoma", Mol. Vis., 13:1783-92 (2007).
Jones and Rhee, "Corticosteroid-induced ocular hypertension and glaucoma: a brief review and update of the literature", Curr. Opin. Ophthalmol., 17:163-7 (2006).
Kompella, et al., "Recent advances in ophthalmic drug delivery", Ther. Deliv., 1:435-56 (2010).
Kompella, et al., "Subconjunctival nano- and microparticles sustain retinal delivery of budesonide, a corticosteroid capable of inhibiting VEGF expression", Invest. Ophthalmol Vis Sci., 44:1192-1201 (2003).
McGhee, et al., "Locally administered ocular corticosteroids—Benefits and risks", Drug Saf., 25: 33-55 (2002).
Nance, et al., "A dense poly(ethylene glycol) coating improves penetration of large polymeric nanoparticles within brain tissue", Sci. Transl. Med. 4:149ra119 (2012).
Ng, Ocular Anatomy and Physiology (2nd ed.), Optometry Vis Sci., 86:1208 (2009).
Nguyen, et al., "Long-term topical steroid treatment improves graft survival following normal-risk penetrating keratoplasty", Am. J. Ophthalmol., 144:318-9 (2007).
Pai, et al., "Current concepts in intravitreal drug therapy for diabetic retinopathy", Saudi J. Ophthalmol., 24:143-9 (2010).
Proia, et al., "The effect of angiostatic steroids and beta-cyclodextrin tetradecasulfate on corneal neovascularization in the rat", Exp. Eye. Res., 57:693-8 (1993).
Randleman, et al., "Prevention and treatment of corneal graft rejection: Current practice patterns (2004)", Cornea, 25:286-90 (2006).
Rautio, et al., "Prodrugs: design and clinical applications", Nat. Rev. Drug Discov., 7:255-70 (2008).
Reimondez-Troitiño, et al., "Nanotherapies for the treatment of ocular diseases", Eu. J. Pharm. Biopharm., 95:279-93 (2015).

(56) References Cited

OTHER PUBLICATIONS

Rhen and Cidlowski, "Antiinflammatory action of glucocorticoids—New mechanisms for old drugs", N. Engl. J. Med., 353:1711-23 (2005).
Seguro, et al., "Long-term complications of past glucocorticoid use", Autoimmun. Rev., 12:629-32 (2013).
Shelke, et al., "Intravitreal poly(L-lactide) microparticles sustain retinal and choroidal delivery of TG-0054, a hydrophilic drug intended for neovascular diseases", Drug Deliv. Transl. Res., 1:76-90 (2011).
Shimazaki, et al., "Efficacy and safety of long-term corticosteroid eye drops after penetrating keratoplasty: A prospective, randomized, clinical trial", Ophthalmol., 119:668-73 (2012).
Tabbara, "Pharmacologic strategies in the prevention and treatment of corneal transplant rejection", Int. Ophthalmol., 28:223-32 (2008).
Vandervoort, "Ocular drug delivery: nanomedicine applications", Nanomedicine, 2:11-21 (2007).
Wadhwa, et al., "Nanocarriers in ocular drug delivery: An update review", Curr. Pharm. Des., 15:2724-50 (2009).
Weijtens, et al., "Dexamethasone concentration in the subretinal fluid after a subconjunctival injection, a peribulbar injection, or an oral dose", Ophthalmol., 107:1932-8 (2000).
Weijtens, et al., "High concentration of dexamethasone in aqueous and vitreous after subconjunctival injection", Am. J. Ophthalmol., 128:192-7 (1999).
Weijtens, et al., "Intraocular penetration and systemic absorption after topical application of dexamethasone disodium phosphate", Ophthalmol., 109:1887-91 (2002).
Xu, et al., "Nanotechnology approaches for ocular drug delivery", Middle East Afr J. Ophthalmol., 20:26-37 (2013).
Xu, et al., "Scalable method to produce biodegradable nanoparticles that rapidly penetrate human mucus", J. Control. Release, 170(2):279-86 (2013b).
Yang, et al., "Biodegradable nanoparticles composed entirely of safe materials that rapidly penetrate human mucus", Angew. Chem. Int. Ed., 50:2597-2600 (2011).
Zhang, et al,"The effect of corticosteroid and cyclosporin A on murine corneal allograft rejection", Graefes Arch. Clin. Exp. Ophthalmol., 238:525-30 (2000).
International Search Report for corresponding PCT application PCT/US2015/043478 dated Oct. 19, 2015.
Chennamaneni_et al., "Development of a novel bioerodible dexamethasone implant for uveitis and postoperative cataract inflammation", J Control Release, 167(1):53-9 (2013).
Diebold, et al., "Drug delivery systems for ophthalmic administration of anti-inflammatory agents", Anti-Inflammatory & Anti-Allergy Agents in Medicinal Chemistry, 10(3):203-14 (2011) Abstract Only.
Pai, et al., "Current concepts in intravitreal drug therapy for diabetic retinopathy", Saudi J Ophthalmology, 24:143-9 (2010).
Regnier-Delplace, et al., "PLGAs bearing carboxylated side chains: novel matrix formers with improved properties for controlled drug delivery", J Control Release, 166(3):256-67 (2013) Abstract Only.

* cited by examiner in-vitro drug release profile (B) of DSP/PLGA nanoparticles

GLUCOCORTICOID-LOADED NANOPARTICLES FOR PREVENTION OF CORNEAL ALLOGRAFT REJECTION AND NEOVASCULARIZATION

CROSS-REFERENCE TO RELATED APPLICATIONS

This application is a 371 application of International Application No. PCT/US2015/043478 filed Aug. 3, 2015, which claims priority to and benefit of U.S. Provisional Application 62/037,000, filed Aug. 13, 2015, and U.S. Provisional Application No. 62/139,561, filed Mar. 27, 2015, the disclosures of which are hereby incorporated herein by reference in their entirety.

REFERENCE TO SEQUENCE LISTING

The Sequence Listing submitted Aug. 3, 2015 as a text file named "JHU_C12604 PCT_ST25.txt," created on Jul. 31, 2015, and having a size of 2,762 bytes is hereby incorporated by reference.

FIELD OF THE INVENTION

The present invention relates to polymeric controlled release formulations for the delivery of an effective amount of one or more Glucocorticoids to the eye, as well as methods of use thereof for the treatment and prevention of diseases, particularly for the treatment or prevention of graft rejection.

BACKGROUND OF THE INVENTION

The cornea is an avascular, transparent connective tissue, serving as the refractive surface and a protective barrier of the eye. Corneal neovascularization (NV) is caused by a disruption of the balance between angiogenic and antiangiogenic factors. Pathological conditions, such as infection, inflammation, trauma and degenerative disorders can induce the invasion of new blood vessels from the limbus to the normally avascular cornea. Corneal NV can cause lipid exudation, persistent inflammation and corneal scarring, and eventually leading to the loss of corneal transparency and decreased visual acuity. Corneal NV was regarded as one high risk factor for corneal graft failure in keratoplasty surgeries.

Treatments for corneal neovascularization include argon laser photocoagulation, photodynamic therapy, Diathermy and cautery, non-steroidal anti-inflammatory drugs, anti-vascular epithelial growth factor ("VEGF") agents, metalomatrix protease ("MMP") inhibitors and corticosteroids. The mainstay of corneal neovascularization treatment is still the topical corticosteroid. Corticosteroids are potent anti-inflammatory drugs that are used to treat various immune and inflammatory diseases, including the eye. Corticosteroids have been shown to have potent anti-angiogenic function, and various corticosteroids have been widely used to treat ocular neovascularization. Intravitreal corticosteroids or steroid implants have been applied to treat neovascular age-related macular degeneration and diabetic retinopathy in patients because steroids reduce inflammation, and also exhibit antiangiogenic properties and block the up-regulation of vascular endothelial growth factor (VEGF) (Augustin, et al. Current therapies, Clin. Ophthalmol. 3 (2009) 175-182; Pai, et al., Saudi J. Ophthalmol. 24 (2010) 143-149). The anti-angiogenic effect for corneal NV was confirmed in different animal models and in the clinical practice. The cauterization induced corneal neovascularization was effectively inhibited by topical dexamethasone (Proia, et al. Exp. Eye. Res. 57 (1993) 693-698). The IL-1beta induced corneal angiogenesis was believed to be inhibited partially through the blockage of NF-kB signaling for the efficacy of dexamethasone to inhibit corneal neovascularization.

Topical corticosteroid eye drops are the most widely used and convenient for patients. However, the absorption and retention of topically applied drugs, including the corticosteroids, are very poor owing to rapid clearance from ocular surface through the blinking, lacrimation, tear turnover and drainage. Furthermore, the intact corneal structure compromises the peinleation and penetration of drug molecules. Therefore, eye drops exhibit very low ocular bioavailability, and typically less than 5% of the applied dose penetrates through cornea to reach intraocular tissue. Therefore, frequent instillation of eye drops is required to maintain intraocular drug level and achieve therapeutic effect. It can bring in other potential problems including patient compliance and toxicity to ocular surface. High drug level in the anterior chamber up to 4 hours can be achieved through subconjunctival injection of dexamethasone sodium phosphate. Nanotechnologies have been applied to improve ocular drug delivery (Vandervoort, Nanomedicine 2 (2007) 11-21; Reimondez-Troitiño, et al., Eu. J. Pharm. Biopharm Mar. 6, 2015). Nanotechnologies were also used for the treatment of corneal NV (Gonzalez, et al., J. Ocul. Pharmacol. Ther. 29 (2013) 124-134). Nanotechnologies can provide advantages of targeting, overcome ocular barriers, improve the ocular bioavailability, controlled release, reduced side effects, etc.

Corneal transplantation is the oldest and the most common form of solid tissue transplantation, and is widely used to treat cornea failure. Every year about 36,000 cases of corneal transplantation surgeries are performed in the United States. The 2-year graft survival rate at avascular and non-inflamed "low-risk" cornea beds can be up to 90%, however, the rate can be as low as 50% at "high risk" cornea beds, which could have previous graft rejection or show neovascularization or inflammation. Cornea graft failure can greatly increase the burden of eye banks for the limited cornea tissues suitable for implantation.

Immunological rejection is one of the main causes of human corneal graft failure. The first year rejection rate on "normal-risk" avascular and non-inflamed bed is close to 20%, and the rate for "high-risk" neovascularized, inflamed recipient bed can be as high as 50%. Treatment with immunosuppressant agents is the normal strategy to improve corneal graft survival after cornea transplantation. Glucocorticoids are the most widely used immunosuppressant agents in clinic, and their efficacy is widely accepted.

Glucocorticoids can be administrated either systemically or through topical instillation. However, long-teali systemic steroids can cause severe side effects, such as cataracts, glaucoma, glucose abnormalities, growth retardation, opportunistic infections and osteoporosis. The quick pre-corneal clearance and the cornea barrier can greatly impair the efficacy of eye drops through the topical instillation. Therefore, frequent topical applications of steroids are required to achieve acceptable results, and it can carry the additional established risks of raised intraocular pressure and cataract.

Immunologic corneal rejection represents the main cause for graft failure. Immunosuppressive therapies with glucocorticoids, antimetabolite (i.e. mycophelonate mofetil), T-cell inhibitors (i.e. cyclosporine A, tacrolimus, FK506), have been applied to patients with cornea transplantation either systemically or through eye drops. Normally eye drops are preferred over the systemic administration after the surgery for long times, ranging from weeks to months, because the eye is the readily accessible organ to drugs, and reduced systemic side effected related to the systemic administration of immunosuppressive agents. However, eye drops still suffer from the problems, such as quick clearance from the pre-ocular surface, and lower drug concentration in anterior chamber, short time of therapeutic window and frequent administration.

Glucocorticoids have been widely used at the controlling cornea graft rejection at both "low-risk" and "high-risk" corneal grafts. The topical glucocorticoids remain "the gold standard" for controlling cornea graft rejection, but it comes with the risk of side effects, such as cataracts, increases in intraocular pressure, wound dehiscence, and bacterial and fungal infections. Subconjunctival (SC) injection of dexamethasone sodium phosphate (DSP) solution has been shown to be more effective to deliver high level of steroid DSP at anterior chamber in comparison to eye drops. Even 24 h later, the DSP level in the anterior humor was still detectable, with the prolonged drug retention in ocular tissue resulting from the depot effect from SC administration. Subconjunctival injection of steroids provides many advantages over topical administration and systemic administration, however, the drug in ocular tissue is still too short to achieve good therapeutic effects with single administration.

In order to treat chronic diseases of the eye, there is a need for long acting methods for delivering Glucocorticoids to the eye. Formulations which provide extended delivery will minimize the potential for toxicity associated with the administration of many Glucocorticoids. In addition, reducing the need for frequent injections will decrease the risk of endophthalmitis and decrease the burden of frequent clinic visits, a major hardship for patients and their families.

Therefore, it is an object of the invention to provide formulations of Glucocorticoids with improved efficacy.

SUMMARY OF THE INVENTION

Glucocorticoids are the most widely used immunosuppressive agents at controlling cornea rejection. Frequent topical instillation of glucocorticoids eye drops is required because of the rapid ocular clearance. It can cause problems with poor patient compliance and severe side effects. It has been discovered that Biodegradable polymeric particles densely coated with hydrophilic polymer and encapsulating a glucocorticoid such as a glucocorticoid complexed by chelation of metal ions with phosphate or carboxyl groups to the polymer forming the nanoparticles, glucocorticoid complexed to carboxy end groups at the terminus of the polymer, and a water soluble salt of the glucocorticoid, have been developed which provide sustained release of glucocorticoid for up to seven days in vitro, can be administered through subconjunctival (SC) injection and are retained in the conjunctiva tissue of the eye for two weeks. The examples demonstrate the advantages of nanoparticles encapsulating a glucocorticoid such as dexamethasone sodium phosphate (DSP) into a matrix such as biodegradable poly(lactic-co-glycolic acid) (PLGA) which is densely coated with hydrophilic polymer such as PEG or PLURONIC® F127, which exhibit sustained release of DSP for up to 7 days in vitro. DSP-loaded PLGA nanoparticles (DSP-NP) can be easily administered through subconjunctival (SC) injection and retained in the conjunctiva tissue for prolonged period up to 2 weeks. Free DSP solution after SC injection is typically cleared within the first 2 hours, and there is almost no detectable DSP in ocular tissues after 24 hours. In comparison, DSP-NP can provide sustained level of DSP in ocular tissues, including anterior chamber and vitreous, over the 7 days study period. In the preferred embodiment, the glucocorticoid is complexed by chelation of metal ions with phosphate or carboxyl groups in the glucocorticoid and the biodegradable polymer in the nanoparticles. High drug loading, slow release, etc. are obtained using the multi-carboxyl group containing polymers; and preparing the DSP-loaded microspheres (solid-in-oil-in-water emulsion method) which have been found to greatly increase drug loading and slow down the release rate. In one embodiment the particles are microparticles having a diameter up to 100 microns. In another embodiment, the particles are nanoparticles.

As demonstrated by the examples, the DSP-NP formulation injected SC weekly in the rat corneal allograft rejection model showed significantly greater efficacy as compared to saline control, empty particles, and free DSP solution. Most grafts were rejected within 2 weeks when treated with saline or empty nanoparticles. With the DSP treated group, grafts were all rejected after 4 weeks post-surgery. All the cornea grafts remain clear and non-rejected through the whole 9-week study period when they are treated with DSP-NP. These results demonstrate that nanoparticles with sustained release of glucocorticoids can effectively prevent the corneal allograft rejection through SC administration. the monthly injection of DSP-PLA2COOH nanoparticles for corneal rejection As demonstrated by the examples, this biodegradable nanoparticle formulation providing sustained release of corticosteroid dexamethasone sodium phosphate (DSP) can provide effective inhibition of corneal neovascularization, uveitis, and may assist in the treatment of glaucoma. The particles can be injected into the eye at the time of surgery, and then also periodically thereafter. In a preferred embodiment for preventing corneal neovascularization, the particles are injected subconjunctiva. In a preferred embodiment for treatment of uveitis (pan uveitis or the intermediate/posterior uveitis) the particles are injected periocular injection, allowing high drug level in the vitreous. DSP-NP subconjunctival injection can prevent LPS induced uveitis through the retina inflammatory cytokine level measurement. Intermediate and posterior uveitis is difficult to be treated with topical eye drops, and the less invasive periocular injection (including the subconjunctival injection) is advantageous over the more invasive intravitreal injection.

BRIEF DESCRIPTION OF THE DRAWINGS

FIG. 4A is at the injection site; FIG. 4B in the aqueous humor; FIG. 4C in the vitreous humor; and FIG. 4D in the blood. *, p<0.05; , p<0.01; *, p<0.001.

FIG. 16A, aqueous; FIG. 16B, vitreous; FIG. 16C, blood; and FIG. 16D, injection site control.

FIGS. 17A, 17D are transparency score; FIGS. 17B, 17E are edema score, and 17C, 17F are neovascularization.

DETAILED DESCRIPTION OF THE INVENTION

I. Definitions

Figure 1:
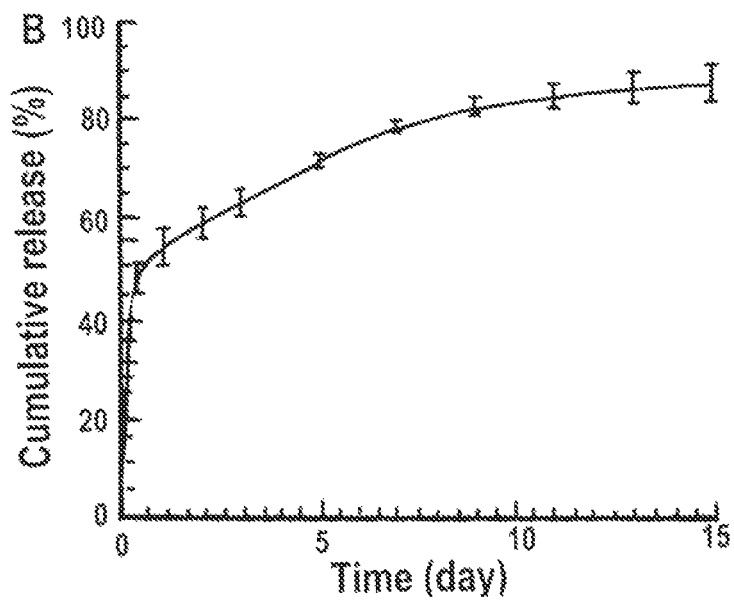
FIG. 1 is a graph of the in vitro drug release profile of DSP/PLGA nanoparticles, plotting cumulative release (%) over time (days).

"Active Agent," as used herein, refers to a physiologically or pharmacologically active substance that acts locally and/or systemically in the body. An active agent is a substance that is administered to a patient for the treatment (e.g., therapeutic agent), prevention (e.g., prophylactic agent), or diagnosis (e.g., diagnostic agent) of a disease or disorder. "Ophthalmic Drug" or "Ophthalmic Active Agent", as used herein, refers to an agent that is administered to a patient to alleviate, delay onset of, or prevent one or more symptoms of a disease or disorder of the eye, or diagnostic agent useful for imaging or otherwise assessing the eye.

"Effective amount" or "therapeutically effective amount," as used herein, refers to an amount of polymeric nanoparticle effective to alleviate, delay onset of, or prevent one or more symptoms, particularly of a disease or disorder of the eye. In the case of age-related macular degeneration, the effective amount of the polymeric nanoparticle delays, reduces, or prevents vision loss in a patient.

"Biocompatible" and "biologically compatible," as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

"Biodegradable Polymer," as used herein, generally refers to a polymer that will degrade or erode by enzymatic action and/or hydrolysis under physiologic conditions to smaller units or chemical species that are capable of being metabolized, eliminated, or excreted by the subject. The degradation time is a function of polymer composition, morphology, such as porosity, particle dimensions, and environment.

"Hydrophilic," as used herein, refers to the property of having affinity for water. For example, hydrophilic polymers (or hydrophilic polymer segments) are polymers (or polymer segments) which are primarily soluble in aqueous solutions and/or have a tendency to absorb water. In general, the more hydrophilic a polymer is, the more that polymer tends to dissolve in, mix with, or be wetted by water.

"Hydrophobic," as used herein, refers to the property of lacking affinity for, or even repelling water. For example, the more hydrophobic a polymer (or polymer segment), the more that polymer (or polymer segment) tends to not dissolve in, not mix with, or not be wetted by water.

Hydrophilicity and hydrophobicity can be spoken of in relative terms, such as but not limited to a spectrum of hydrophilicity/hydrophobicity within a group of polymers or polymer segments. In some embodiments wherein two or more polymers are being discussed, the term "hydrophobic polymer" can be defined based on the polymer's relative hydrophobicity when compared to another, more hydrophilic polymer.

"Nanoparticle," as used herein, generally refers to a particle having a diameter, such as an average diameter, from about 10 nm up to but not including about 1 micron, preferably from 100 nm to about 1 micron. The particles can have any shape. Nanoparticles having a spherical shape are generally referred to as "nanospheres".

"Microparticle," as used herein, generally refers to a particle having a diameter, such as an average diameter, from about 1 micron to about 100 microns, preferably from about 1 micron to about 50 microns, more preferably from about 1 to about 30 microns. The microparticles can have any shape. Microparticles having a spherical shape are generally referred to as "microspheres".

"Molecular weight," as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Mean particle size," as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution" are used interchangeably herein and describe a population of nanoparticles or microparticles where all of the particles are the same or nearly the same size. As used herein, a monodisperse distribution refers to particle distributions in which 90% or more of the distribution lies within 15% of the median particle size, more preferably within 10% of the median particle size, most preferably within 5% of the median particle size.

"Pharmaceutically Acceptable," as used herein, refers to compounds, carriers, excipients, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Branch point," as used herein, refers to a portion of a polymeric nanoparticle that serves to connect multiple hydrophilic polymer segments to one end of the hydrophobic polymer segment or multiple hydrophobic polymer segments to one end of the hydrophilic segment.

"Glucocorticoid," as used herein, refers to, a drug that reduces the level of HIF-1 and/or its ability to stimulate the transcription of genes that contain a hypoxia response element in their promoter region.

"Implant," as generally used herein, refers to a polymeric device or element that is structured, sized, or otherwise configured to be implanted, preferably by injection or surgical implantation, in a specific region of the body so as to provide therapeutic benefit by releasing one or more Glucocorticoids over an extended period of time at the site of implantation. For example, intraocular implants are polymeric devices or elements that are structured, sized, or otherwise configured to be placed in the eye, preferably by injection or surgical implantation, and to treat one or more diseases or disorders of the eye by releasing one or more Glucocorticoids over an extended period. Intraocular implants are generally biocompatible with physiological conditions of an eye and do not cause adverse side effects. Generally, intraocular implants may be placed in an eye without disrupting vision of the eye.

Ranges of values defined herein include all values within the range as well as all sub-ranges within the range. For example, if the range is defined as an integer from 0 to 10, the range encompasses all integers within the range and any and all subranges within the range, e.g., 1-10, 1-6, 2-8, 3-7, 3-9, etc.

II. Polymer-Glucoglucocorticoid Particles

In some embodiments, one or more Glucoglucocorticoids are dispersed or encapsulated in a polymeric matrix for delivery to the eye. The polymeric matrix can be formed from non-biodegradable or biodegradable polymers; however, the polymer matrix is preferably biodegradable. The polymeric matrix can be formed into implants, microparticles, nanoparticles, or combinations thereof for delivery to the eye. Upon administration, the one or more Glucocorticoids are released over an extended period of time, either upon degradation of the polymer matrix, diffusion of the one or more inhibitors out of the polymer matrix, or a combination thereof. By employing a polymeric nanoparticle, particles can be formed with more controlled drug loading and drug release profiles.

In some embodiments, the controlled-release formulation contains particles formed from one or more polymeric nanoparticles. The polymeric nanoparticles are block copolymers containing one or more Glucocorticoids. Typically, the block copolymers contain Glucocorticoid one or more hydrophobic polymer segments, and one or more hydrophilic polymer segments. In certain cases, one or more hydrophilic polymer segments are attached to the one or more hydrophobic polymer segments by a branch point. By employing a polymeric nanoparticle, particles can be formed with more controlled drug loading and drug release profiles. In addition, the solubility of the conjugate can be controlled so as to minimize soluble drug concentration and, therefore, toxicity.

The polymeric nanoparticles contain one or more Glucocorticoids, preferably complexed by chelation of metal ions with phosphate or carboxyl groups, most preferably carboxy end groups at the terminus of the biodegradable polymer such as a polymer containing an ester or other hydrolysable moiety. The glucocorticoid may be derivatized into a water soluble salt, and then incorporated into the polymeric nanoparticle.

A. Glucocorticoids

Glucocorticoids are a group of anti-inflammatory steroid-like compounds, such as hydrocortisone, that are produced by the adrenal cortex, are involved in carbohydrate, protein and fat metabolism, and are used as anti-inflammatory agents. The following is a list of common glucoglucocorticoids in order of relative potency. Glucocorticoids available have different potencies, for example 1 mg of dexamethasone is as effective as 25 mg of hydrocortisone. The following table indicates the relative potency of the main products:

Relative Potency of Glucocorticoid
Hydrocortisone 1
Prednisone 4
Prednisolone 4
Methylprednisolone 5
Triamcinolone 5
Dexamethasone 25
Betamethasone 25
Cortivazol 50

There are many other glucocorticoids including aclometasone, budesonide, clobetasol, clobetasone, desonide, fluocinolone, fluocortolone flunisolide, fluticasone, methylprednisolone, mometasone, paramethasone, rimexolone, and tixocortols. Most situations involving graft rejection utilize the more potent compounds, such as dexamethasone or betamethasone.

The water soluble glucocorticoid salts may be obtained commercially or synthesized using conventional chemistry. Preferred salts include phosphates, such as dexamethasone sodium phosphate and hydrocortisone sodium phosphate and carboxylates such as hydrocortisone sodium succinate and methylprednisolone sodium succinate, B. Polymers Forming the Nanoparticles Polymeric nanoparticles can contain one or more polymer, homopolymers or copolymers. In preferred embodiments, the polymer is a biodegradable polymer. In cases where the hydrophobic polymer is biodegradable, the polymer degradation profile may be selected to influence the release rate of the active agent in vivo. For example, the polymer can be selected to degrade over a time period from seven days to 2 years, more preferably from seven days to 56 weeks, more preferably from four weeks to 56 weeks, most preferably from eight weeks to 28 weeks.

Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(hydroxyalkanoates); poly (lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

In the preferred embodiment the polymer is a polyhydroxy ester such as poly lactic acid, poly glycolic acid or a copolymer thereof. The ratio of glycolic acid to lactic acid can be optimized to control the rate of degradation.

The polymer can be a polyanhydride. The polyanhydride can be an aliphatic polyanhydride, an unsaturated polyanhydride, or an aromatic polyanhydride. Representative polyanhydrides include polyadipic anhydride, polyfumaric anhydride, polysebacic anhydride, polymaleic anhydride, polymalic anhydride, polyphthalic anhydride, polyisophthalic anhydride, polyaspartic anhydride, polyterephthalic anhydride, polyisophthalic anhydride, poly carboxyphenoxypropane anhydride, polycarboxyphenoxyhexane anhydride, as well as copolymers of these polyanhydrides with other polyanhydrides at different mole ratios. Other suitable polyanhydrides are disclosed in U.S. Pat. Nos. 4,757,128, 4,857,311, 4,888,176, and 4,789,724. The polyanhydride can also be a copolymer containing polyanhydride blocks. In certain embodiments, the polymer is polysebacic anhydride. In certain embodiments, the polymer is poly(1,6-bis(p-carboxyphenoxy) hexane-co-sebacic acid) (poly(CPH-SA). In certain embodiments, the polymer is poly(1,3-bis(p-carboxyphenoxy) propane-co-sebacic acid) (poly(CPP-SA).

The molecular weight of the hydrophobic polymer can be varied to prepare polymeric nanoparticles that form particles having properties, such as drug release rate, optimal for specific applications. The polymer can have a molecular weight of about 150 Da to 1 MDa. In certain embodiments, the polymer has a molecular weight of between about 1 kDa and about 100 kDa, more preferably between about 1 kDa and about 50 kDa, most preferably between about 1 kDa and about 25 kDa.

C. Hydrophilic Polymers

The nanoparticles are coated with a hydrophilic polymer. These must be hydrophilic, biocompatible (i.e., it does not induce a significant inflammatory or immune response), non-toxic polymers or copolymers. Examples of suitable polymers may include poly(alkylene glycols) such as polyethylene glycol (PEG), poly(propylene glycol) (PPG), and copolymers of ethylene glycol and propylene glycol, poly (oxyethylated polyol), poly(olefinic alcohol), poly(vinyl alcohol), and copolymers, terpolymers, and mixtures thereof.

In preferred embodiments, the one or more hydrophilic polymer segments contain a poly(alkylene glycol) chain. The poly(alkylene glycol) chains may contain between 8 and 500 repeat units, more preferably between 40 and 500 repeat units. Suitable poly(alkylene glycols) include polyethylene glycol), polypropylene 1,2-glycol, poly(propylene oxide), polypropylene 1,3-glycol, and copolymers thereof. In certain embodiments, the one or more hydrophilic polymer segments are PEG chains. In such cases, the PEG chains can be linear or branched, such as those described in U.S. Pat. No. 5,932,462. In certain embodiments, the PEG chains are linear.

Each of the one or more hydrophilic polymer segments can independently have a molecular weight of about 300 Da to 1 MDa. The hydrophilic polymer segment may have a molecular weight ranging between any of the molecular weights listed above. In certain embodiments, each of the one or more hydrophilic polymer segments has a molecular weight of between about 1 kDa and about 20 kDa, more preferably between about 1 kDa and about 15 kDa, most preferably between about 1 kDa and about 10 kDa. In a preferred embodiment, each of the one or more hydrophilic polymer segments has a molecular weight of about 5 kDa.

Not all hydrophilic polymers are effective. As demonstrated by the examples, the preferred polymer is the PLURONIC® F127 sold by BASF. PLURONICS® are triblock copolymers composed of one polypropylene oxide ("PPO") block connected to two polyethylene oxide ("PEO") blocks. The PEO blocks dissolve well in aqueous media because they are mostly hydrophilic while the PPO block does not dissolve because it is mostly hydrophobic at ambient temperature.

III. Synthesis of Polymeric Nanoparticles

Polymeric nanoparticles can be prepared using synthetic methods known in the art. Representative methodologies for the preparation of polymeric nanoparticles are discussed below. The appropriate route for synthesis of a given polymeric nanoparticle can be determined in view of a number of factors, such as the structure of the polymeric nanoparticle, the identity of the polymers which make up the conjugate, the identity of the active agent, as well as the structure of the compound as a whole as it relates to compatibility of functional groups, protecting group strategies, and the presence of labile bonds.

Polymeric implants (e.g., rods, discs, wafers, etc.), microparticles, and nanoparticles for the controlled delivery of one or more Glucocorticoids are provided, dispersed or encapsulated in a matrix. In some embodiments, the particles or implants contain one or more Glucocorticoids dispersed or encapsulated in a polymeric matrix.

The particles can be provided as a mixture of two or more different polymeric nanoparticles. For example, particles may be formed from two or more polymeric nanoparticles containing different Glucocorticoids. In other cases, the particles are formed from two or more polymeric nanoparticles containing the same Glucocorticoid, to vary the release rate of Glucocorticoids.

Particles having an average particle size of between 10 nm and 1000 microns are useful in the compositions described herein. In preferred embodiments, the particles have an average particle size of between 10 nm and 100 microns, more preferably between about 100 nm and about 50 microns, more preferably between about 200 nm and about 50 microns. In certain embodiments, the particles are nanoparticles having a diameter of between 500 and 700 nm. The particles can have any shape but are generally spherical in shape.

In some embodiments, the population of particles formed from one or more polymeric nanoparticles is a monodisperse population of particles. In other embodiments, the population of particles formed from one or more polymeric nanoparticles is a polydisperse population of particles. In some instances where the population of particles formed from one or more polymeric nanoparticles is polydisperse population of particles, greater that 50%, 60%, 65%, 70%, 75%, 80%, 85%, 90%, or 95% of the particle size distribution lies within 10% of the median particle size.

Preferably, particles formed from one or more polymeric nanoparticles contain significant amounts of a hydrophilic polymer, such as PEG, on their surface.

Microparticle and nanoparticles can be formed using any suitable method for the formation of polymer micro- or nanoparticles known in the art. The method employed for particle formation will depend on a variety of factors, including the characteristics of the polymers present in the polymeric nanoparticle or polymer matrix, as well as the desired particle size and size distribution. The type of Glucocorticoid(s) being incorporated in the particles may also be a factor as some Glucocorticoids are unstable in the presence of certain solvents, in certain temperature ranges, and/or in certain pH ranges.

In circumstances where a monodisperse population of particles is desired, the particles may be formed using a method which produces a monodisperse population of nanoparticles. Alternatively, methods producing polydisperse nanoparticle distributions can be used, and the particles can be separated using methods known in the art, such as sieving, following particle formation to provide a population of particles having the desired average particle size and particle size distribution.

Common techniques for preparing microparticles and nanoparticles include, but are not limited to, solvent evaporation, hot melt particle formation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

The polymeric nanoparticles contain one or more Glucocorticoids, preferably complexed by chelation of metal ions with phosphate or carboxyl groups, most preferably carboxy end groups at the terminus of the biodegradable polymer such as a polymer containing an ester or other hydrolysable moiety, as described in the examples. The glucocorticoid may be derivatized into a water soluble salt, and then incorporated into the polymeric nanoparticle.

Intraocular implants may be spherical or non-spherical in shape. For spherical-shaped implants, the implant may have a largest dimension (e.g., diameter) between about 5 µm and about 2 mm, or between about 10 µm and about 1 mm for administration with a needle, greater than 1 mm, or greater than 2 mm, such as 3 mm or up to 10 mm, for administration by surgical implantation. If the implant is non-spherical, the implant may have the largest dimension or smallest dimension be from about 5 µm and about 2 mm, or between about 10 µm and about 1 mm for administration with a needle, greater than 1 mm, or greater than 2 mm, such as 3 mm or up to 10 mm, for administration by surgical implantation.

The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. The implant may be a cylindrical pellet with a length of about 7 mm to about 10 mm, and a diameter of about 0.75 mm to about 1.5 mm. In certain embodiments, the implant is in the form of an extruded filament with a diameter of about 0.5 mm, a length of about 6 mm, and a weight of approximately 1 mg. In some embodiments, the dimension are, or are similar to, implants already approved for intraocular injection via needle: diameter of 460 microns and a length of 6 mm and diameter of 370 microns and length of 3.5 mm.

Intraocular implants may also be designed to be least somewhat flexible so as to facilitate both insertion of the implant in the eye, such as in the vitreous, and subsequent accommodation of the implant. The total weight of the implant is usually about 250 to 5000 µg, more preferably about 500-1000 µg. In certain embodiments, the intraocular implant has a mass of about 500 µg, 750 µg, or 1000 µg.

Implants can be manufactured using any suitable technique known in the art. Examples of suitable techniques for the preparation of implants include solvent evaporation methods, phase separation methods, interfacial methods, molding methods, injection molding methods, extrusion methods, coextrusion methods, carver press method, die cutting methods, heat compression, and combinations thereof. Suitable methods for the manufacture of implants can be selected in view of many factors including the properties of the polymer/polymer segments present in the implant, the properties of the one or more Glucocorticoids present in the implant, and the desired shape and size of the implant. Suitable methods for the preparation of implants are described, for example, in U.S. Pat. No. 4,997,652 and U.S. Patent Application Publication No. US 2010/0124565.

In certain cases, extrusion methods may be used to avoid the need for solvents during implant manufacture. When using extrusion methods, the polymer/polymer segments and Glucocorticoid are chosen so as to be stable at the temperatures required for manufacturing, usually at least about 85 degrees Celsius. However, depending on the nature of the polymeric components and the one or more Glucocorticoids, extrusion methods can employ temperatures of about 25° Celsius to about 150° Celsius, more preferably about 65° Celsius to about 130° Celsius. Implants may be coextruded in order to provide a coating covering all or part of the surface of the implant.

IV. Pharmaceutical Formulations

Pharmaceutical formulations contain one or more polymeric nanoparticles in combination with one or more pharmaceutically acceptable excipients. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions.

A. Additional Active Agents

In addition to the one or more Glucocorticoids present in the polymeric particles, the formulation can contain one or more additional therapeutic, diagnostic, and/or prophylactic agents. The active agents can be a small molecule active agent or a biomolecule, such as an enzyme or protein, polypeptide, or nucleic acid. Suitable small molecule active agents include organic and organometallic compounds. In some instances, the small molecule active agent has a molecular weight of less than about 2000 g/mol, more preferably less than about 1500 g/mol, most preferably less than about 1200 g/mol. The small molecule active agent can be a hydrophilic, hydrophobic, or amphiphilic compound.

In some cases, one or more additional active agents may be encapsulated in, dispersed in, or otherwise associated with particles formed from one or more polymeric nanoparticles. In certain embodiments, one or more additional active agents may also be dissolved or suspended in the pharmaceutically acceptable carrier.

In the case of pharmaceutical compositions for the treatment of ocular diseases, the formulation may contain one or more ophthalmic drugs. In particular embodiments, the ophthalmic drug is a drug used to treat, prevent or diagnose a disease or disorder of the posterior segment eye. Non-limiting examples of ophthalmic drugs include anti-glaucoma agents, anti-angiogenesis agents, anti-infective agents, anti-inflammatory agents, growth factors, immunosuppressant agents, anti-allergic agents, and combinations thereof.

Representative anti-glaucoma agents include prostaglandin analogs (such as travoprost, bimatoprost, and latanoprost), beta-adrenergic receptor antagonists (such as timolol, betaxolol, levobetaxolol, and carteolol), alpha-2 adrenergic receptor agonists (such as brimonidine and apraclonidine), carbonic anhydrase inhibitors (such as brinzolamide, acetazolamine, and dorzolamide), miotics (i.e., parasympathomimetics, such as pilocarpine and ecothiopate), seretonergics muscarinics, dopaminergic agonists, and adrenergic agonists (such as apraclonidine and brimonidine).

Representative anti-angiogenesis agents include, but are not limited to, antibodies to vascular endothelial growth factor (VEGF) such as bevacizumab (AVASTIN®) and rhuFAb V2 (ranibizumab, LUCENTIS®), and other anti-VEGF compounds including aflibercept (EYLEA®); MACUGEN® (pegatanim sodium, anti-VEGF aptamer or EYE001) (Eyetech Pharmaceuticals); pigment epithelium derived factor(s) (PEDF); COX-2 inhibitors such as celecoxib (CELEBREX®) and rofecoxib (VIOXX®); interferon alpha; interleukin-12 (IL-12); thalidomide (THALOMID®) and derivatives thereof such as lenalidomide (REVLIMID®); squalamine; endostatin; angiostatin; ribozyme inhibitors such as ANGIOZYME® (Siena Therapeutics); multifunctional antiangiogenic agents such as NEOVASTAT® (AE-941) (Aeterna Laboratories, Quebec City, Canada); receptor tyrosine kinase (RTK) inhibitors such as sunitinib (SUTENT®); tyrosine kinase inhibitors such as sorafenib (Nexavar®) and erlotinib (Tarceva®); antibodies to the epidermal grown factor receptor such as panitumumab (VECTIBIX®) and cetuximab (ERBITUX®), as well as other anti-angiogenesis agents known in the art.

Anti-infective agents include antiviral agents, antibacterial agents, antiparasitic agents, and anti-fungal agents. Representative antiviral agents include ganciclovir and acyclovir. Representative antibiotic agents include aminoglycosides such as streptomycin, amikacin, gentamicin, and tobramycin, ansamycins such as geldanamycin and herbimycin, carbacephems, carbapenems, cephalosporins, glycopeptides such as vancomycin, teicoplanin, and telavancin, lincosamides, lipopeptides such as daptomycin, macrolides such as azithromycin, clarithromycin, dirithromycin, and erythromycin, monobactams, nitrofurans, penicillins, polypeptides such as bacitracin, colistin and polymyxin B, quinolones, sulfonamides, and tetracyclines.

In some cases, the active agent is an anti-allergic agent such as olopatadine and epinastine.

Anti-inflammatory agents include both non-steroidal and steroidal anti-inflammatory agents. Suitable steroidal active agents include glucocorticoids, progestins, mineralocorticoids, and glucocorticoids.

The ophthalmic drug may be present in its neutral form, or in the form of a pharmaceutically acceptable salt. In some cases, it may be desirable to prepare a formulation containing a salt of an active agent due to one or more of the salt's advantageous physical properties, such as enhanced stability or a desirable solubility or dissolution profile.

Generally, pharmaceutically acceptable salts can be prepared by reaction of the free acid or base forms of an active agent with a stoichiometric amount of the appropriate base or acid in water or in an organic solvent, or in a mixture of the two; generally, non-aqueous media like ether, ethyl acetate, ethanol, isopropanol, or acetonitrile are preferred. Pharmaceutically acceptable salts include salts of an active agent derived from inorganic acids, organic acids, alkali metal salts, and alkaline earth metal salts as well as salts formed by reaction of the drug with a suitable organic ligand (e.g., quaternary ammonium salts). Lists of suitable salts are found, for example, in Remington's Pharmaceutical Sciences, 20th ed., Lippincott Williams & Wilkins, Baltimore, Md., 2000, p. 704. Examples of ophthalmic drugs sometimes administered in the form of a pharmaceutically acceptable salt include timolol maleate, brimonidine tartrate, and sodium diclofenac.

In some cases, the active agent is a diagnostic agent imaging or otherwise assessing the eye. Exemplary diagnostic agents include paramagnetic molecules, fluorescent compounds, magnetic molecules, and radionuclides, x-ray imaging agents, and contrast media.

In certain embodiments, the pharmaceutical composition contains one or more local anesthetics. Representative local anesthetics include tetracaine, lidocaine, amethocaine, proparacaine, lignocaine, and bupivacaine. In some cases, one or more additional agents, such as a hyaluronidase enzyme, is also added to the formulation to accelerate and improves dispersal of the local anesthetic.

B. Formulations for Ocular Administration

The polymeric nanoparticles will preferably be formulated as a suspension for injection to the eye. Pharmaceutical formulations for ocular administration are preferably in the form of a sterile aqueous s suspension of particles formed from one or more polymeric nanoparticles. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

In some instances, the formulation is distributed or packaged in a liquid form. Alternatively, formulations for ocular administration can be packed as a solid, obtained, for example by lyophilization of a suitable liquid formulation. The solid can be reconstituted with an appropriate carrier or diluent prior to administration.

Solutions, suspensions, or emulsions for ocular administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for ocular administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for ocular administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for ocular administration may also contain one or more excipients known art, such as dispersing agents, wetting agents, and suspending agents.

V. Methods of Use

Controlled release dosage formulations for the delivery of one or more glucocorticoids can be used to treat or a disease or disorder in a patient associated with vascularization, such as acute macular degeneration, inflammation, such as corneal graft rejection, or retinitis. Upon administration, the one or more Glucocorticoids are released over an extended period of time at concentrations which are high enough to produce therapeutic benefit, but low enough to avoid cytotoxicity.

In one preferred embodiment, the pharmaceutical compositions are administered to treat or prevent a disease or disorder in a patient associated with ocular neovascularization.

In another preferred embodiment, the formulations are administered through subconjunctival (SC) injection and retained in the conjunctiva tissue, to treat or prevent corneal graft rejection.

When administered to the eye, the particles release a low dose of one or more glucosteroids and/or other active agents over an extended period of time, preferably longer than 3, 7, 10, 15, 21, 25, 30, or 45 days. The structure of the polymeric nanoparticle or makeup of the polymeric matrix, particle morphology, and dosage of particles administered can be tailored to administer a therapeutically effective amount of one or more active agents to the eye over an extended period of time while minimizing side effects, such as the reduction of scoptopic ERG b-wave amplitudes and/or retinal degeneration.

The formulations can be administered locally to the eye by intravitreal injection (e.g., front, mid or back vitreal injection), subconjunctival injection, intracameral injection, injection into the anterior chamber via the temporal limbus, intrastromal injection, injection into the subchoroidal space, intracorneal injection, subretinal injection, and intraocular injection. In a preferred embodiment, the pharmaceutical composition is administered by intravitreal injection.

The implants can be administered to the eye using suitable methods for implantation known in the art. In certain embodiments, the implants are injected intravitreally using a needle, such as a 22-gauge needle. Placement of the implant intravitreally may be varied in view of the implant size, implant shape, and the disease or disorder to be treated.

In preferred embodiments, the nanoparticles are administered locally to the eye by intravitreal injection (e.g., front, mid or back vitreal injection), subconjunctival injection, intracameral injection, injection into the anterior chamber via the temporal limbus, intrastromal injection, injection into the subchoroidal space, intracorneal injection, subretinal injection, and intraocular injection.

In preferred embodiments, the nanoparticles are administered in an effective amount to prevent or decrease neovascularization, graft rejection, or inflammation such as uveitis.

In a preferred embodiment, the nanoparticles are administered no less frequently than once a week, once every two weeks, once every four weeks, once a month, once every two months, or once every three months.

In some embodiments, the pharmaceutical compositions and/or implants described herein are co-administered with one or more additional active agents. "Co-administration", as used herein, refers to administration of the controlled release formulation of one or more Glucocorticoids with one or more additional active agents within the same dosage form, as well as administration using different dosage forms simultaneously or as essentially the same time. "Essentially at the same time" as used herein generally means within ten minutes, preferably within five minutes, more preferably within two minutes, most preferably within in one minute.

In some embodiments, the pharmaceutical compositions and/or implants described herein are co-administered with one or more additional treatments for a neovascular disease or disorder of the eye. In some embodiments, the pharmaceutical compositions and/or implants described herein are co-administered with one or more anti-angiogenesis agent such bevacizumab (AVASTIN®), ranibizumab, LUCENTIS®, or aflibercept (EYLEA®).

Preferably, the particles will release an effective amount of one or more Glucocorticoids over an extended period of time to prevent or reduce inflammation. In preferred embodiments, the particles release an effective amount of one or more Glucocorticoids over a period of at least two weeks, more preferably over a period of at least four weeks, more preferably over a period of at least six to eight weeks. In some embodiments, the particles release an effective amount of one or more Glucocorticoids over a period of three months or longer.

The present invention will be further understood by reference to the following non-limiting examples.

EXAMPLES

Example 1: Preparation of PLGA Nanoparticles for Delivery of Glucocorticoid

Materials and Method
Preparation of PLGA Nanoparticles
Alexa Fluor 555 (AF555) cadaverine and Alexa Fluor 647 (AF647) cadaverine (Invitrogen, Carlsbad, Calif.), used here as fluorescent markers, were chemically conjugated to PLGA (MW 3.2 kDa, LA:GA=50:50) (SurModics Pharmaceuticals, Birmingham, Ala.). Nanoparticles composed of labeled or unlabeled PLGA polymers were prepared by a solvent diffusion (or nanoprecipitation) method. Briefly, 20 mg of the polymer was dissolved in 1 mL of tetrahydrofuran (THF), and added dropwise to 40 ml of ultrapure water under magnetic stirring at 700 rpm. After stirring for about 1 h, the solution was rotoevaporated for 30 min to remove the residual THF. The particles were collected by centrifuging at 10,000 g for 25 min, and resuspended in 0.2 mL of ultrapure water. For PLURONICS® F127-coated particles, the ultrapure water was replaced with 5% F127 aqueous solutions during the nanoprecipitation. The PLGA nanoparticles coated with F127 (PLGA/F127) were washed with 1% F127 by centrifugation at 10,000 g for 25 min, and resuspended in 0.2 mL of ultrapure water. Size and zeta-potential (surface charge) were measured by dynamic light scattering and laser Doppler anemometry, respectively, using a ZETASIZER NANO® ZS90 (Malvern Instruments, Southborough, Mass.).

Preparation of Model Nanoparticles

Red fluorescent COOH-modified PS particles of 100, 200, 500, 1000 nm (Molecular Probes) and 5 µm (Bangs Laborites, Inc.) in size were covalently modified with methoxy (MeO)-PEG-amine ($NH_2$) (MW 5 kD; Creative PEGWorks) by COOH-amine reaction. PEGylated PS particles (PS-PEG) were thoroughly washed, resuspended in water and stored at +4° C. ready for use. PS-PEG particles were characterized in terms of surface charge and hydrodynamic diameter, and their physicochemical characteristics were reported in Table 3.

Preparation of DSP-Loaded PLGA Nanoparticles

Dexamethasone 21-phosphate sodium salt (DSP) (Sigma Aldrich, St. Louis, Mo.) was encapsulated into PLGA nanoparticles with F127 coatings following a modified solvent diffusion method. Briefly, a DSP-zinc complex was formed by adding 1 mL of 0.5 M zinc acetate aqueous solution to 0.5 mL of an aqueous solution containing 10 mg of DSP. After centrifuging at 10,000 g for 5 min, the precipitated complex and 50 mg PLGA (MW 3.2 kDa, LA:GA=50:50) were dissolved in 2.5 mL of THF followed by the addition of 20 µL of triethanolamine (TEOA, Sigma Aldrich, St. Louis, Mo.). The mixture was added dropwise into 100 mL of 5% F127 solution with stirring to form DSP-loaded PLGA nanoparticles coated with F127 (DSP/PLGA/F127 or DSP-NP). After complete removal of the THF by solvent evaporation and rotoevaporation, 1 mL of 0.5 M ethylenediaminetetraacetic acid (EDTA, Sigma Aldrich, St. Louis, Mo.) aqueous solution (pH 7.5) was added to the nanoparticle suspension to chelate zinc and solubilize any unencapsulated DSP-zinc complexes. The nanoparticles were collected by centrifugation at 10,000 g for 25 min, washed twice with 1% F127, and resuspended in 0.2 mL of ultrapure water. The hydrodynamic size and surface charge of nanoparticles were characterized as described above. Particle morphology was visualized using a Hitachi H-7600 transmission electron microscope (Hitachi Co. Ltd., Tokyo, Japan).

Drug Loading and In Vitro Drug Release Study

To measure the DSP content in DSP/PLGA/F127 nanoparticles, approximately 50 µL of PLGA nanoparticles was freeze-dried, weighed and dissolved in 0.5 mL of acetonitrile. Subsequently, 1 mL of 50 mM EDTA was added, to chelate zinc and solubilize encapsulated DSP, and the DSP concentration in the solution was measured by reverse phase HPLC. Isocratic separation was performed on a Shimadzu Prominence LC system (Kyoto, Japan) equipped with a Pursuit 5 C18 column (Varian Inc, Lake Forest, Calif.) and mobile phase consisting of acetonitrile/water (35/65 v/v) containing 0.1% trifluoroacetic acid (flow rate=1 mL/min). Column effluent was monitored by UV detection at 241 nm. The drug loading (LD) and encapsulation efficiency (EE) were calculated according to the following equations:

$$DL\ (\%) = (amount\ of\ DSP\ in\ nanoparticles/weight\ of\ nanoparticles) \times 100$$

$$EE\ (\%) = (drug\ loading\ measured/theoretical\ drug\ loading) \times 100$$

To measure the in vitro release profile of DSP, four hundred µL of the nanoparticle suspension was sealed in a dialysis tubing cellulose membrane (MW cutoff: 10 kDa, Sigma Aldrich, St. Louis, Mo.). The sealed dialysis membrane was placed into a 50 mL conical tube containing 12 mL of release media (PBS, pH 7.4) and incubated at 37° C. on a platform shaker (140 rpm). The entire release media was collected at predetermined intervals and replaced with 12 mL of fresh PBS. DSP concentration in the collected release media was measured by HPLC as described above.

Animals

Eight-week-old male Sprague Dawley, Lewis, and Brown Norway rats were purchased from Harlan (Indianapolis, Ind.). Sprague Dawley rats were used for in vivo safety and retention study. Lewis rats were used as the receptor animals, and Brown-Norway rats were used as donor animals. All rats were cared in accordance with the Association for Research in Vision and Ophthalmology Resolution concerning the use of animals in ophthalmological research. Animals were anesthetized before experimental procedures. All experimental protocols were approved by the Johns Hopkins Animal Care and Use Committee.

Retention of Nanoparticles Following Subconjunctival Administration

The retention of nanoparticles after SC injection was investigated by imaging the whole eye on the Xenogen IVIS Spectrum optical imaging system (Caliper Life Sciences Inc., Hopkinton, Mass.). Rats were anesthetized with an intramuscular injection of a mixture of Ketamine (80 mg/kg) and Xylazine (8 mg/kg). Non-degradable model particles, PS-PEG NP with red fluorescence (dynamic diameter around 100 nm, 200 nm, 500 nm, 1 µm and 5 µm), were injected to Sprague Dawley rats by SC injection (50 µL) using a 26-gauge needle. The eye lids were expanded with a 45 G speculum (Focus Ophthalmics, LLC, Ontario, Calif.) during imaging. The total fluorescence counts in the injection site were recorded at excitation wavelength of 550 nm and emission wavelength of 570 nm. The images were analyzed by the Living Image software, and the retention of nanoparticles was quantified through comparing to the eye with SC injection of nanoparticles at 0 h. Rat eyes without treatment were used as baseline.

The retention of biodegradable PLGA/F127 nanoparticles after SC injection was carried out and analyzed at the same way described above. PLGA/F127 nanoparticles with chemically conjugated Alexa Fluo 647 (AF647) dye were used, and the whole eye was imaged with an excitation wavelength of 640 nm and emission wavelength of 680 nm.

In Vivo Safety Profile of Unloaded PLGA Nanoparticles

Empty PLGA nanoparticles, both F127-coated and uncoated, were administered in saline (50 µL) by SC injection at a dose of 1 mg per eye (n=9). Control eyes were treated with saline (n=9). At time points of 2 day, 7 day and 14 day, animals were sacrificed and whole eyes together with conjunctiva tissue were harvested for histology study after fixation and staining with H&E.

In Vivo Ocular DSP Levels after SC Injection

In order to detect the ocular DSP level after SC injection in rats, [3H]-labeled DSP spiked with DSP (10 µCi:1 mg DSP) during the preparation of F127-coated DSP-loaded PLGA nanoparticles (DSP-NP). Nanoparticles were suspended in saline at 20 µCi/mL. The free DSP solution at 20 µCi/mL was prepared at the same blending ratio. 40 µL (~0.8 µCi per eye) of same formulation was injected to both eyes of the same animal (Sprague Dawley rat). At the indicated time intervals, 2 h, 1 day, 3 day, 5 day and 7 day after injection, the rats were anesthetized by intramuscular injection of ketamine/xylazine solution. The animal was sacrificed after collecting two drops of blood from the tail vein.

The eye ball with conjunctiva tissue was carefully removed from rats and rinsed with PBS, dried by Kimwipe tissue. The anterior chamber humor, cornea, vitreous, retina and the remaining eye ball tissue were carefully dissected and collected. Both cornea and retina tissues were rinsed with PBS and dried with Kimwipe tissue. All the samples were weighed, dissolved with 2 mL of Solvable by incubation at 50° C. overnight. Blood samples were bleached with 0.2 ml $H_2O_2$ and 20 µL, 0.5M EDTA. 10 ml Ultimold gold scintillation medium was added before counting the radioactivity in a scintillation counter. The results were expressed as a percentage of the injected dose and are the mean±sd of four eyes (2 animals) per data point. The level of DSP in blood was the average of two animals per time point. Total percentage of injected dose at the periocular tissue and the radioactivity per mg (or mL) of tissue were calculated.

Cornea Transplantation Surgery

All procedures performed with rats were approved by the Johns Hopkins University Animal Care and Use Committee. The Brown-Norway donor rats were sacrificed and the central corneal button of both eyes were removed with a 4.0-mm trephine and kept in physiological solution ready for use. The surgery was performed by a corneal surgeon (QP) under an operating microscope. The cornea recipient Lewis rats were anesthetized with an intramuscular injection of a mixture of Ketamine (80 mg/kg) and Xylazine (8 mg/kg). Repeated instillations of 0.5% tropicamide eye drops were used on Lewis rats for total pupil dilation before surgery. A paracentesis was performed before trephinization, and the anterior chamber was filled with hyaluronic acid. The corneal buttons were removed from the receptor Lewis rats with a 3.5-mm trephine. The donor corneal button was sutured to receptor cornea with 8 suture points.

Postoperative Treatments Followed Penetrating Keratoplasty (PK)

Immediately after the penetrating keratoplasty, the animals were randomly divided into 5 groups: group 1 (4 rats) received with subconjunctival injection of 50 µL saline, group 2 (5 rats) received with SC injection of 50 µl empty NP, group 3 (5 rats) received with SC injection of 50 µL DSP solution at concentration of 1 mg/mL and group 4 (6 rats) received with SC injection of 50 µL, DSP-loaded nanoparticles (DSP-NP) at concentration of 1 mg DSP/mL. All groups of animals were undertaken same treatment once every week until the failure of grafts or the end point of study (9 week).

The clinical observations with a slit lamp microscope were performed by two ophthalmologists (QP and LT) on post-operational (PO) 2 week for group 1 and group 2, PO 4 week for group 3 and PO 9 week for group 4. Three parameters were evaluated for the examination of the corneal grafts (cornea transparency, edema and neovascularization). The scoring for the parameters is presented below.

Intraocular pressure was monitored at PO 2 day, 1 week, 2 week, 4 week, 6 week, 8 week and 9 week after the surgery. IOP recorded for each eye is the average of three successful measurements. Animals at the end time points were sacrificed by $CO_2$ and the eyes with PK surgery were enucleated. Eye tissues were fixed with 10% formalin for 24 h before embedding in paraffin. Sections (5 µm) were cut from through the direction of optical nerve and cornea, and stained with H&E.

Statistical Analysis

Statistical analysis of data was performed by one-way analysis of variance (ANOVA) followed by Tukey's test. Differences were considered to be statistically significant at a level of $P<0.05$.

Results

Preparation and Characterization of DSP-Loaded PLGA Nanoparticles

It is difficult to encapsulate the hydrophobic dexamethasone into PLGA nanoparticles because of the incompatibility of dexamethasone and PLGA. The water-soluble prodrug, dexamethasone 21-phosphate disodium (DSP), can be converted to parent drug dexamethasone in vivo mainly facilitated by phosphatases, present in all organs including the ocular tissues. The water-soluble DSP is efficiently co-encapsulated with zinc into PLGA nanoparticles in the presence of PLURONICS® F127. The physicochemical properties of DSP-loaded PLGA nanoparticles (DSP-NP) are shown in Table 3. DSP-NP exhibited a surface charge of −5 mV indicating a dense PEG coating, which attributes to the strong binding of PLURONICS F127 on hydrophobic nanoparticles. DSP-NP was spherical in morphology confirmed by TEM observation. DSP-NP exhibited a high drug loading of ~12% w/w, corresponding to an encapsulation efficiency of ~72%. The release of DSP from DSP-NP is in a sustained manner up to 15 days, and nearly 80% of loaded DSP was released within the first 7 days (FIG. 1). It was believed that zinc increased both the encapsulation efficiency and promoted the sustained release of water-soluble glucocorticoid from PLGA nanoparticles because of the formation of an ionic bridge between the terminal carboxyl groups on PLGA and the phosphate groups on the drug molecules.

TABLE 1

Evaluation of Clinical Parameters after Transplantation (score 0-4)

| Clinical Parameters | | Score | | | |
|---|---|---|---|---|---|
| | 0 | 1 | 2 | 3 | 4 |
| Cornea transparency | clear cornea | slight opacity | mild opacity with iris details visible | moderate opacity with iris details not visible | severe opacity, white cornea |
| Edema | none | Slight | moderate stromal edema | marked stromal edema | severe |

TABLE 1-continued

Evaluation of Clinical Parameters after Transplantation (score 0-4)

| Clinical Parameters | Score | | | | |
|---|---|---|---|---|---|
| | 0 | 1 | 2 | 3 | 4 |
| Neovascularization | no observable grown of new vessels | new vessels invading <1/3 of the recipient bed | new vessel invading <2.3 of the recipient bed | new vessels growing up to the limiting ring of the graft | new vessels invading graft |

The Ocular Retention of Nanoparticles after SC Administration

Figure 2:
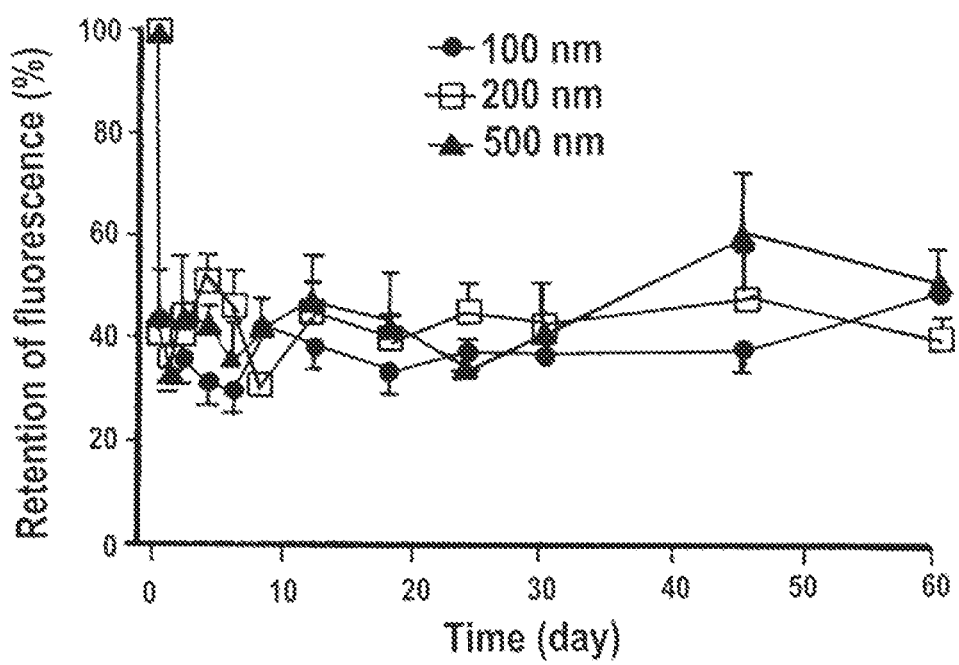
FIG. 2 is a graph of the percent retention of non-degradable polystyrene particles (100 nm, 200 nm, 500 nm, 1 micron, 5 microns) with a PS-PEG coating after subconjunctival ('SC') injection into rats over time (days), quantified by Zenogen IVIS Spectrum optical imaging of fluorescent after subcutaneous administration to rats.

The fluorescence images of normal rat eyes and with SC injection of fluorescence dye labeled nanoparticles showed the retention of non-degradable polystyrene particles with bioinert PEG coating (PS-PEG) after SC injection to rats. The retention of PS-PEG particles were quantified by Xenogen IVIS Spectrum optical imaging. Live imaging was used to quantify the retention of nanoparticles after SC administration in rats. First, non-degradable PS-PEG particles were applied to investigate the size effect on the retention of nanoparticles. PS-PEG particles with size of 100 nm, 200 nm, 500 nm, 1 µm and 5 µm were all shown near neutral surface charge indicating a dense PEG coating. PS-PEG particles were administered to rats through SC injection, and the fluorescence signal was quantified with live imaging. PS-PEG particles with sizes of 100 nm, 200 nm and 500 nm all exhibited approximately 60% decrease of fluorescence signal during the first 6 h after the SC injection. Afterwards, a constant level of fluorescence was observed for the remaining 2-month retention study, indicating a constant retention of these non-degradable particles after SC injection for particle as small as 100 nm. For large particles (1 µm and 5 µm), nearly 100% retention of particles were observed through the whole retention study (FIG. 2). However, it was more difficult to inject large particles through the 26 gauge needle. Some sedimentation and aggregation of nanoparticles were observed even though these particles were PEGylated and were well suspended before injection.

Representative fluorescence images at different time points and the retention curve of rat eyes after SC injection of AF-647 labeled PLGA/F127 NP were used to calculate the retention of biodegradable PLGA/F127 nanoparticles (186 nm) after SC injection. Fluorescent dyes were chemically conjugated to PLGA before the preparation of PLGA/F127 nanoparticles. Fluorescence signal was detected even after PO 30 day. A gradual decrease of the signal was observed during the whole 30 days retention study. Less than 10% of fluorescence signal was retained at PO 8 day.

The Ocular Safety of PLGA Nanoparticles after SC Injection

Sample cornea histology at PO 2 day, 7 day and 14 day of representative images of rat cornea and conjunctiva tissues treated with SC injection of saline, PLGA/F127 and uncoated PLGA nanoparticles showed conjunctiva tissues close to the injection area had chronic inflammation (grade 1) at PO 2 day for PLGA/F127 NP and PLGA NP, and the chronic inflammation gradually disappeared at PO 7 day and PO 14 day (grade 0-1). Similar inflammation responses were observed for saline control groups. Saline injection showed mild chronic inflammation (grade 1) at PO 2 day, and recovered at PO 7 day and PO 14 days (grade 0-1). (Observed and graded by Pathologist Dr. Charles Eberhart, the full grade of inflammation is 0-3, no-inflammation to severe inflammation).

Figure 3:
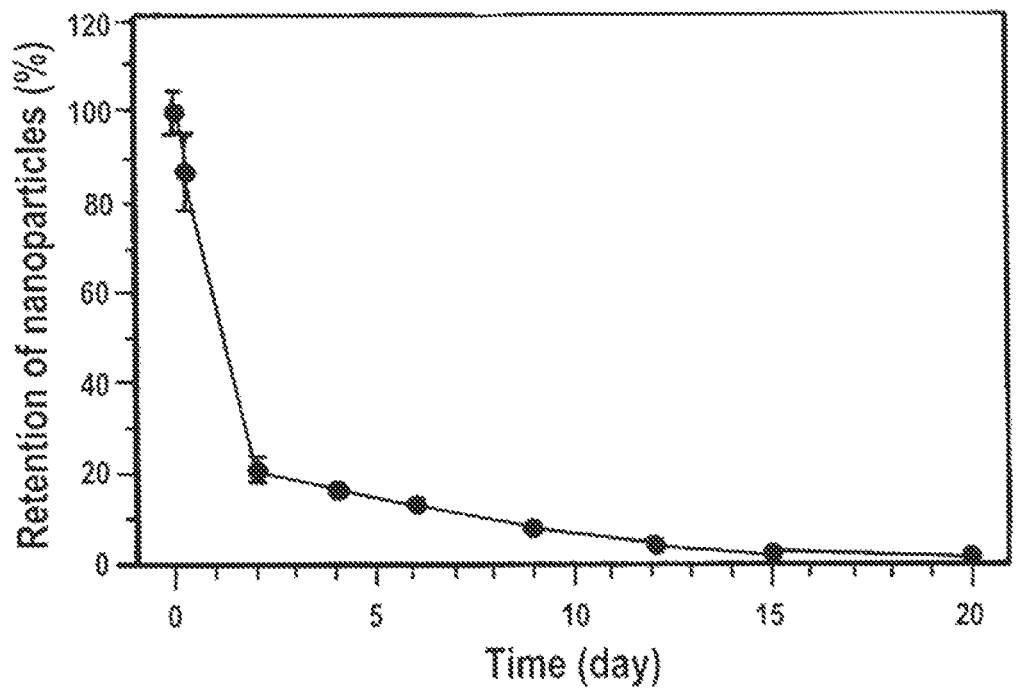
FIG. 3 is a graph of percent retention in eyes over time (days) of PLGA/F127 nanoparticles injected SC into rats. This value may be affected by the cleavage of the dye from polymer chain.

In order to determine the in vivo toxicity of empty nanoparticles carriers, PLGA (no PEG coating), PLGA/F127 (dense-PEG coating) nanoparticles suspended in saline were administered to healthy Sprague Dawley rats through SC injection. Histological examination was applied to determine the inflammatory responses in the ocular tissues. Only mild inflammation in conjunctiva tissue at day 2 was observed for all injection groups including the saline control group. At day 7 and day 14, all nanoparticles with and without F127 coating did not show inflammation in all the ocular tissues, including the conjunctiva, cornea and retina. Similar to saline control, PLGA/F'127 nanoparticles showed good safety profiles with very mild to none inflammation after the SC injection to rat eyes at day 2, day 7 and day 14. For all the groups, no inflammation was observed in other ocular tissues, including retina, anterior chamber and cornea. Results are shown in FIG. 3.

DSP-NP after SC Administration Sustained DSP Levels in the Ocular Tissues

Figure 4A:
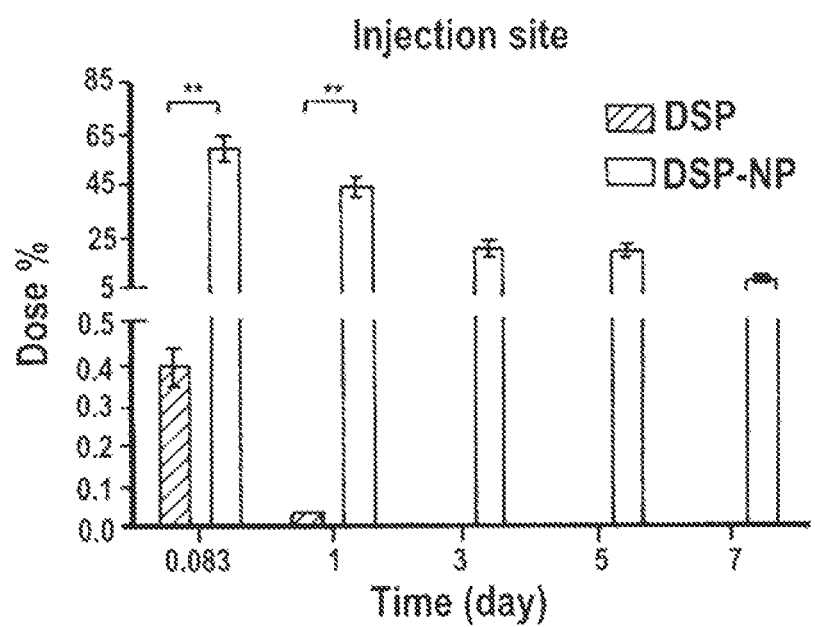
FIGS. 4A-4D are graphs of the pharmacokinetics (DSP/ml over time in days) of free DSP solution and DSP-NP after subcutaneous administration to rats.
Figure 4B:
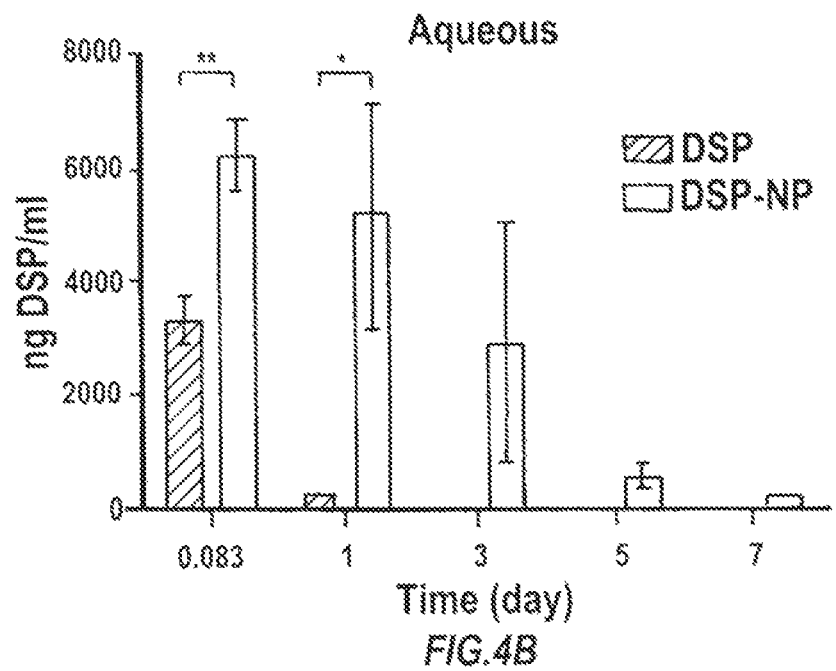
Figure 4C:
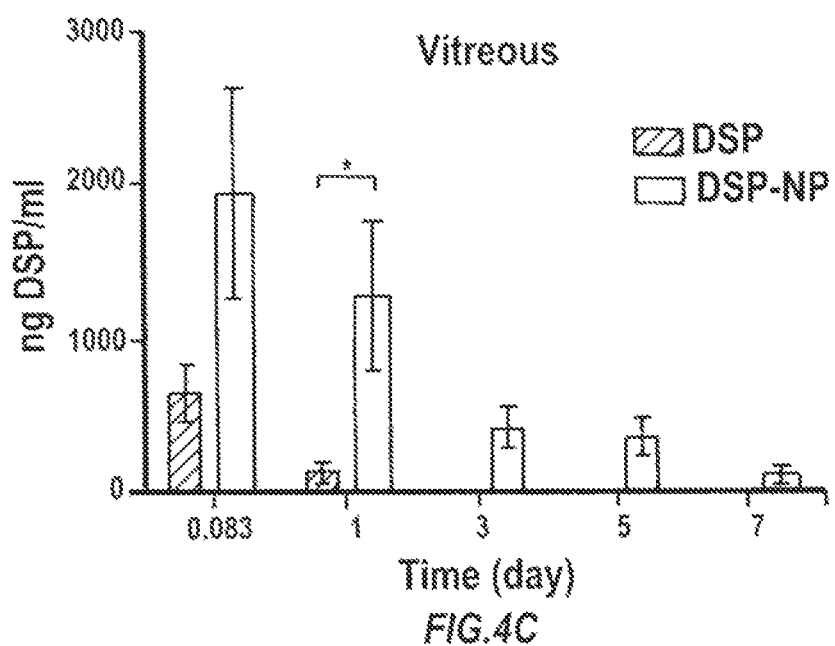
Figure 4D:
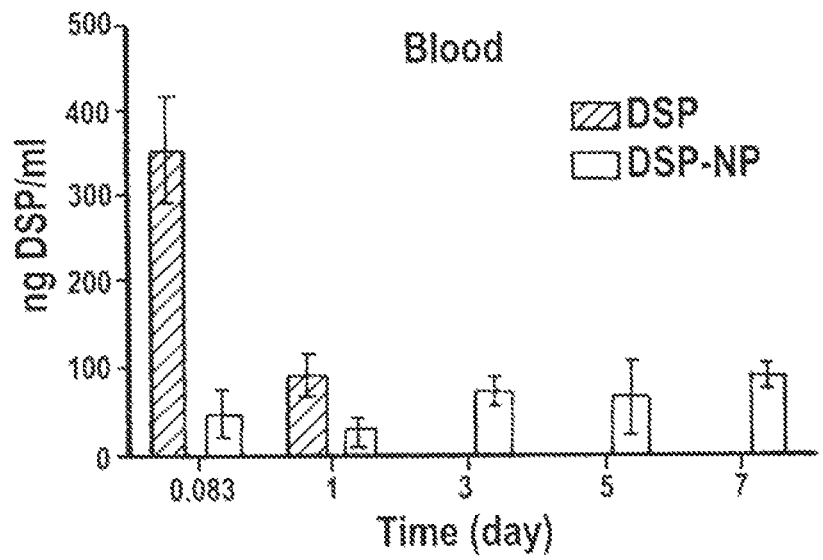

Ocular tissue levels of DSP were compared following a single SC injection of either DSP free drug or DSP-loaded PLGA/F127 nanoparticles (DSP-NP) (both containing ~0.08 mg DSP). FIGS. 4A-4D are graphs of the pharmacokinetics (DSP/ml over time in days) of free DSP solution and DSP-NP after subcutaneous administration to rats. FIG. 4A is at the injection site; FIG. 4B in the aqueous humor; FIG. 4C in the vitreous humor; and FIG. 4D in the blood.

Figure 5:
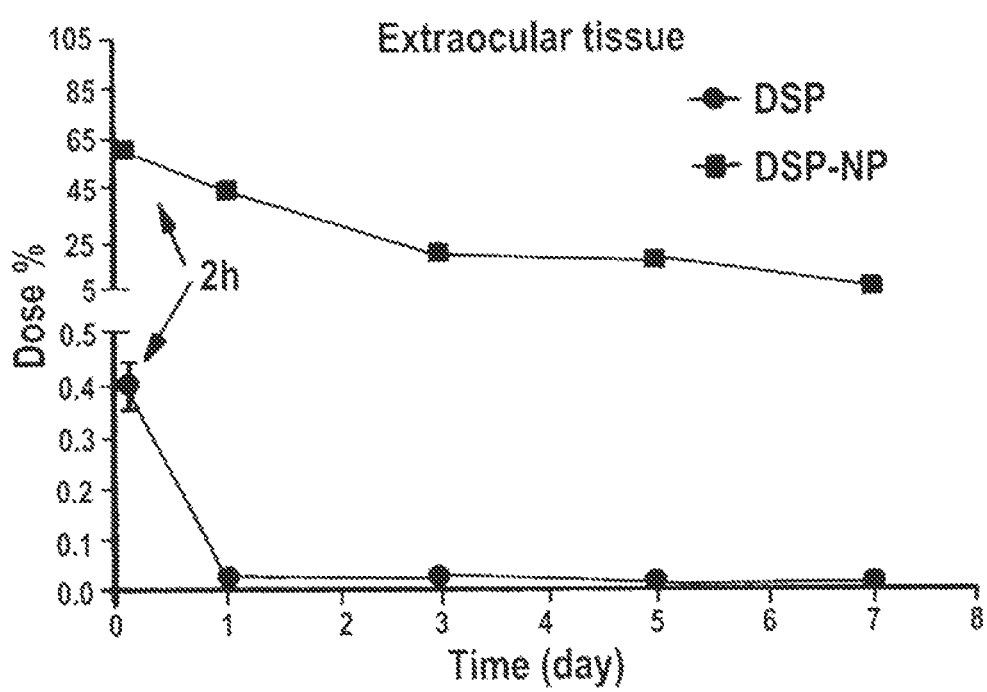
FIG. 5 is a graph of the retained DSP dose, injected alone or encapsulated in NPs, in the extraocular tissue (ocular tissue after the removal of retina, cornea, vitreous and aqueous humor) quantified by measuring the radioactivity of $^3$H-DSP in all tissues. No value at some data points means that the level is not detectable.

Approximately 0.4% of the total dose of free DSP solution was retained at the conjunctiva tissue PO 2 h, and almost no DSP can be detected at PO day 1. In comparison, DSP-NP group showed nearly 65% of the total dose retained at the conjunctiva tissue at PO 2 h, and the retained DSP level at conjunctiva tissue gradually decreased to 5% at PO day 7. By analyzing the ocular tissues, aqueous humor, vitreous, retina and cornea, it was found the DSP levels at ocular tissues diminished very quickly to reach the baseline for SC injection of DSP free drug. The SC injection of DSP-NP significantly prolonged the high level of DSP at aqueous humor and vitreous up to PO day 7. The DSP levels at retina and cornea were very low for both DSP and DSP-NP groups. The DSP levels were also measured in blood samples collected at different time points. DSP-NP groups showed constantly low level of DSP (~50 ng DSP per ml) from PO 2 h to PO 7 day. In comparison, DSP group showed as high as 350 ng DSP per ml at blood at PO 2 h and then quickly diminished to baseline. DSP levels were quantified by measuring the radioactivity of $^3$H-DSP in all the tissues. No value at some data points means that the level is not detectable. This is shown in FIG. 5.

DSP-NP after SC Administration Prevented Corneal Graft Rejection

Postoperative slit-examination of the transplanted corneas with SC injection of nanoparticles was performed. All grafts were rejected for groups with SC injection of saline and SC injection of PLGA/F127 (NP) at PO 2 week. All grafts were rejected for groups with SC injection of DSP (D) at PO 4 week and all grafts stayed clear with SC injection of DSP/PLGA/F127 (DSP-NP) even at the end study point of PO 9 week (E).

Figure 6:
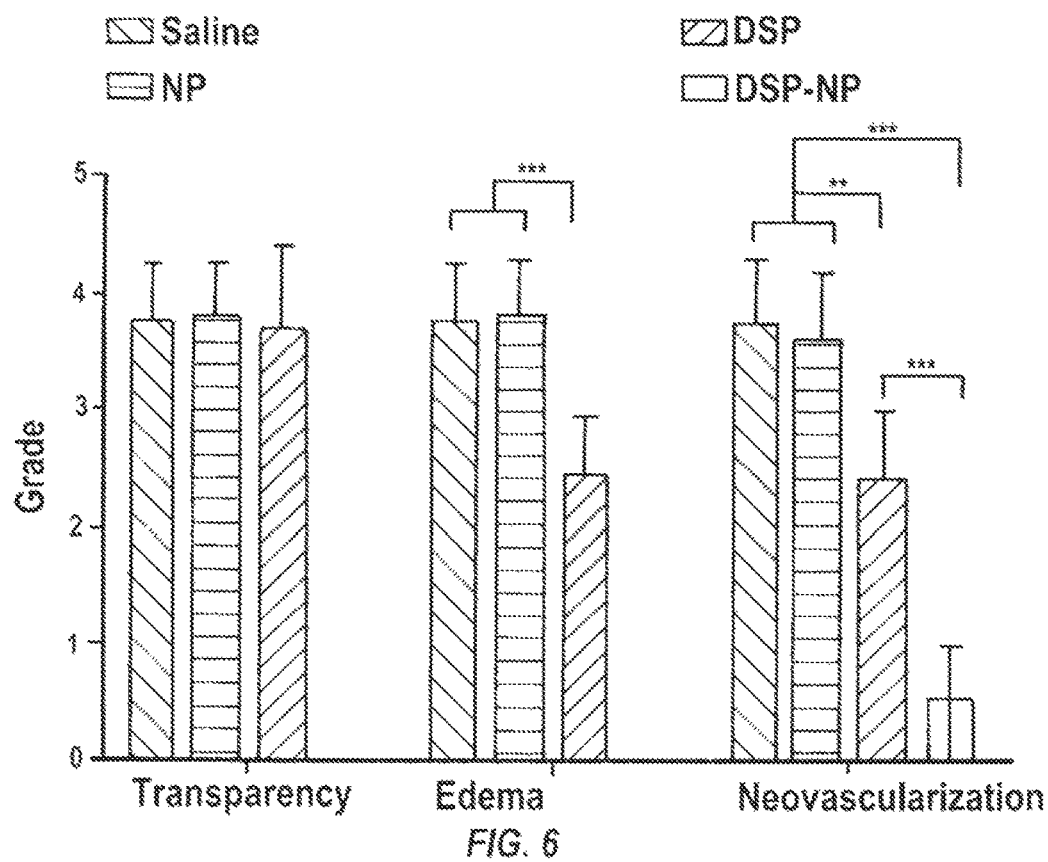
FIG. 6 is a bar graph of the clinical evaluation of grafts treated with SC injection of saline, NPs, DSP or DSP-NP at an end time point in terms of cornea transparency, edema and new blood vessels. No bars shown on transparency and edema for DSP-NP mean that grafts are completely transparent and have no edema.
Figure 7:
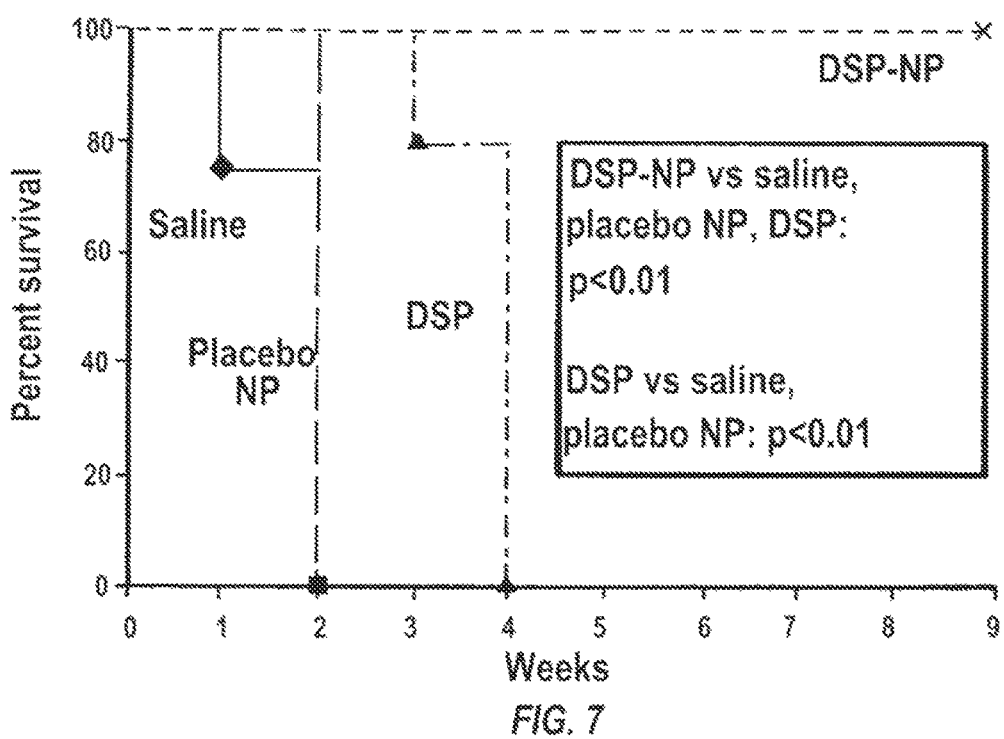
FIG. 7 is a survival curve of transplanted corneal grafts treated with SC injection of saline control, empty NP, free DSP or DSP-NP.

The grafts treated with SC injection of saline, NP, DSP and DSP-NP were clinically evaluated at end time point in terms of cornea transparence, edema and new vessels. Results are shown in FIGS. 6 and 7. No bars in FIG. 6 shown on transparency and edema for DSP-NP mean that grafts are completely transparent and have no edema. Histological images of transplanted corneas after the treatment of saline at PO 2 week, empty NP at PO 2 week, free DSP at PO 4 week and DSP-NP at PO 9 week after SC injections were performed. The surgical procedures were all successfully performed by experienced ophthalmologists, and no surgical complications occurred. Immediately after the PK, animals were randomly divided into 4 groups, and treatments to each group were started by SC injection of saline, NP, DSP and DSP-NP. Three parameters including cornea transparency, edema and neovascularization, were used on clinical observations to score the grafts. At postoperative (PO) 2 week, the saline control and NP control groups exhibited severe edema, cornea grafts were opaque, and large amount of new vessels formed not only around the suture but also into the corneal graft. However, grafts treated with weekly injection of DSP showed significant less edema ($p<0.0001$), and less neovascularization ($p<0.001$). Corneal grafts in DSP group were as opaque as saline control and NP control groups. The DSP-NP treated group showed significantly better results in terms of corneal transparency, edema and neovascularization. There was no edema for DSP-NP treated group, and all cornea grafts in the 6 rats were clear throughout the whole 9 weeks of study.

There were few new vessels occurred around the suture, but the neovascularization in DSP-NP group was significantly less than all other 3 groups ($p<0.05$). Animals were sacrificed when complete corneal graft failure, indicated by severe edema and severe opacity at corneal transparency, was observed.

Figure 8:
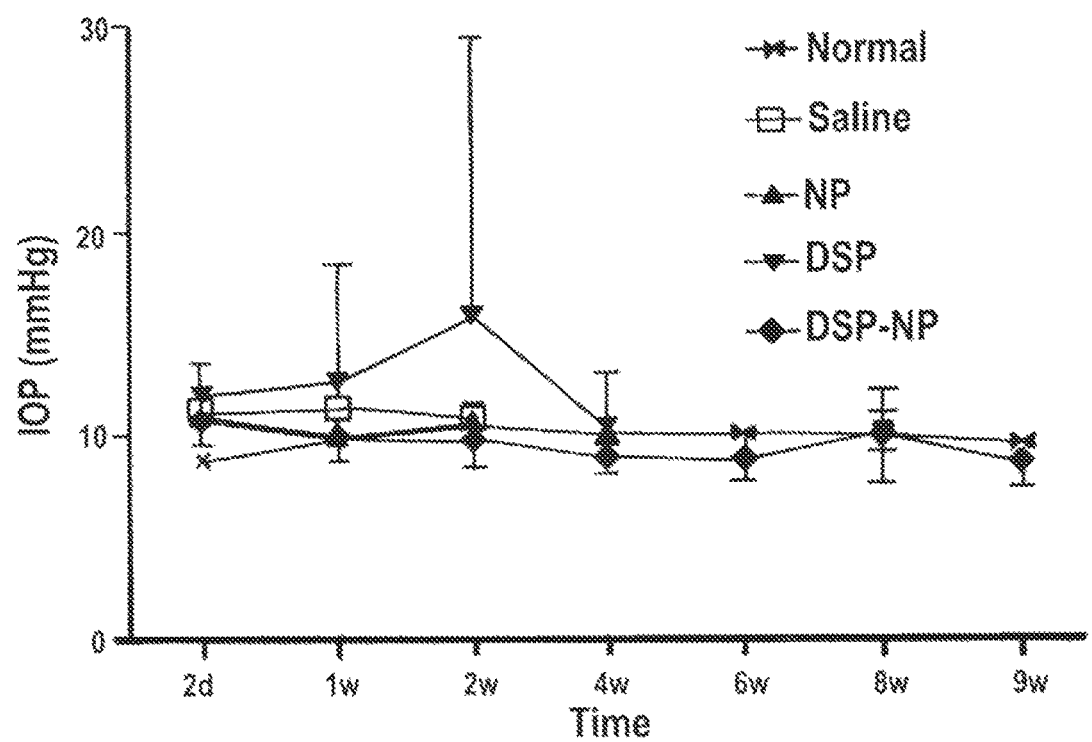
FIG. 8 is a graph of the intraocular pressure (IOP), over time (days or weeks), where the IOP was measured on the eyes with corneal graft transplantation followed by treatment with saline, empty NP, free DSP, or DSP-NP. Normal eyes were used as control.

The survival curve of transplanted cornea grafts treated with SC injection of saline control, empty NP, free DSP and DSP-NP is shown in FIG. 7. Intraocular pressure for the same samples over nine weeks is shown in FIG. 8. Complete graft rejection occurred at PO 2 week for saline control and NP control groups. Slight improvement was achieved by the weekly SC injection of DSP free drugs, and the survival rate of cornea grafts was 100% and 80% at PO 2 week and PO 3 week, respectively. However, all corneas of the DSP group were still rejected at PO 4 week. A significant higher survival rate was observed for DSP-NP treated group with 100% survival rate at the end of the study (PO 9 week). At the PO 9 week, the cornea grafts of DSP-NP group were all clear, transparent, lack of any hints of corneal rejection episode.

Histological examination of the cornea tissues which were acquired at the end points (PO 2 week for saline and NP groups, PO 4 week for DSP group, and PO 9 week for DSP-NP group) showed that cornea tissues for saline, NP and DSP groups were all swollen and thicker than the normal healthy cornea. Neutraphils and macrophages were observed in the cornea tissue for all the three groups. Obvious endothelium cell death for the grafts of all the three control groups was observed, and epithelium layer of cornea grafts lost its integrity at all the three control groups. In comparison, the cornea of DSP-NP treated group showed a complete cornea structure with intact epithelium layer, stroma and endothelium layer, and no swelling of cornea tissue existed. Most importantly, no inflammatory cells were found in DSP-NP treated cornea, revealing that the transplanted cornea survived after the DSP-NP treatment with full function by the SC injection during the whole study, and the grafts start function as normal.

Figure 9A:
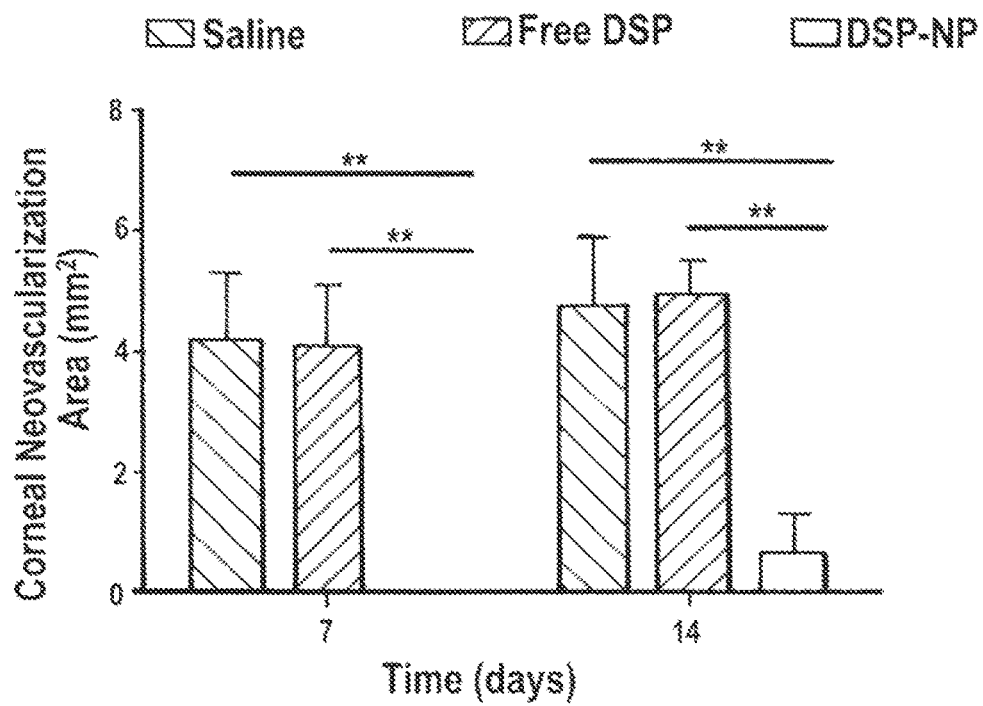
FIGS. 9A-9B are graphs of the quantitative analysis of corneal neovascularization for NV area (FIG. 9A) and vessel length (FIG. 9B) after treatment with SC injection of saline, DSP and DSP-NP.
Figure 9B:
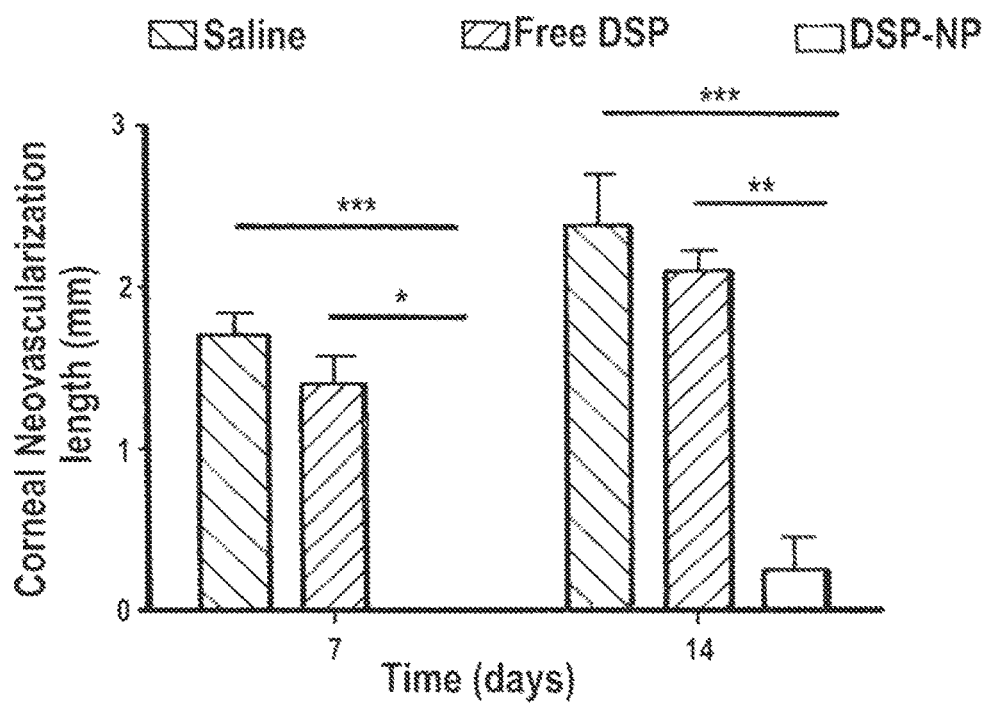

Corneal neovascularization over 14 days for the same groups is shown in FIGS. 9A and 9B.

Summary of Results

Sustained release platforms which can provide immunosuppressant for prolonged time would favor the clinical application, and improve the patient compliance and reduce side effects. Nanoparticles can sustain the release of drugs and have been widely used to deliver therapeutic agents to the eye by various routes, including intravitreal injection, topical administration and subconjunctval injection. Subconjunctival nanoparticles have been shown to sustain release of therapeutic agents from several days to months depending on the applications. The release rate can be modified by the selection of different polymers or change in formulation. A biodegradable nanoparticle platform with dense-PEG coating for sustained release of glucocorticoid to prevent corneal rejection has been developed. Certain PLURONICS®, such as F127, can be readily adsorbed onto PLGA nanoparticles to form dense PEG coatings, which render the particles bioinert. Eyes are very sensitive organs, and irritation, inflammatory responses can be induced by administrated ophthalmological formulations, which can cause un-comfort of patients and even result in serious eye disorders. Thus, a safe platform and route to sustain deliver immunosuppressant agents can be advantageous.

The drug delivery platform of PLGA/F127 comprises PLGA and F127, both classified as Generally Regarded as Safe (GRAS) materials by the FDA and having a long history of use in a variety of pharmaceutical formulations, including in ophthalmological formulations. However, the safety issue on the ophthalmic use of nanoparticles still remains a major concern. In the current study, the inflammatory responses for PLGA/F127 group were comparable to the SC injection of saline control group through all the checked time points (PO 2 day, 7 day and 14 day). Healthy rats elicited a mild ocular inflammation after SC injection during the first 2 days post SC injection, which diminishes within 7 days. The effect of dense coating from F127 on nanoparticles to lower the inflammation has been reported at aspiration to BALB/C mice lung and vaginal administration to CF-1 mice. In SC administration of PLGA nanoparticles both coated and uncoated with F127, no severe inflammation was observed, unlike the studies in lung and vaginal tract. The periocular conjunctiva tissues (mainly comprised of muscles and connective tissues) of SC administration may not be as sensitive as the epithelia involved in lung airways and vaginal tract. The safety property may vary when the PLGA with different coatings applied to other ocular parts. Even though the F127 coating may not add more safety benefits to PLGA nanoparticles for SC administration, the use of F127 can greatly enhance the yield of DSP-NP in comparison to uncoated PLGA NP. Great aggregation occurred for PLGA NP without F127 coating during the nanoparticle collection.

Non-degradable model PS-PEG nanoparticles can be retained after SC injection for up to 2 months. One-hundred nm, 200 nm and 500 nm PS-PEG exhibited a 40-60% drop at the first 6 hours after SC injection, which may result from the leakage after injection. The 50 µL volume of single injection could be too much for the rat subconjucntival space. The hydrophilic PEG coating on nanoparticles may further help the leakage or translocation of particles through the injection site because of the lack of adhesion to the tissues. It has been reported that non-PEGylated hydrophobic PS particles (carboxylate-modified) with 200 nm and 2 μm in size were permanently retained in the subconjunctival tissue after SC injection in 20-30 μL volume. The smaller injection volume and the hydrophobic particle nature may result in less or none leakage of nanoparticles. Very similar results were observed for large particles (1 μm and 5 μm), and very little decrease at ocular retention was monitored. Big particles were easy for sedimentation, and they could be blocked within the conjunctiva tissue when the injected aqueous solution leaked out, and the surface property does not change too much to their retention. Biodegradable PLGA nanoparticles show a similar trend at the first 6 h after the SC injection, and nearly 40% of the dose decreased, but the fluorescence signal kept decreasing for 15 days until the signal complete vanished, which was different from the non-degradable 200 nm PS-PEG nanoparticles. The gradual decrease in the fluorescence signal may result from the degradation of polymer and also the release of chemically conjugated fluorescence dye. Through optimizing the injection conditions, suitable amount of nanoparticles/microparticles can be successfully administered into SC space for the sustained release of therapeutics.

In order to confirm that DSP can be efficiently delivered to anterior chamber and even the vitreous for prolonged period, ocular pharmacokinetic studies were conducted with DSP-NP with the tritium labeled DSP in healthy rats. Free DSP was used as control. Weijtens and coworkers have found that SC injection was the most effective method of delivering DSP into both the anterior and posterior segments of the patients' eye in comparison to either peribulbar injection or oral dose. Previous reports have shown that the SC injection of DSP resulted in peak vitreous dexamethasone concentrations at PO 2-3 h. In the current study, the peak concentration of DSP in aqueous and vitreous in rat eyes was observed two hours after injection for both free DSP and DSP-NP. A very clear trend showed that high concentration of DSP was achieved very quickly within the first 2 hours after injection even though the exact Tmax was not clear based on this study. Subconjunctival injection of DSP results in DSP remaining in the anterior chamber and the vitreous in comparison to the eye drop. With frequent dosing with eye drops, the penetration of DSP into vitreous is negligible and the DSP concentration in the anterior chamber is far lower than the SC injection. However, the SC administration of DSP free drug can only provide effective DSP concentration in anterior chamber for less than 6 hr. There was a big decrease of the DSP levels in anterior chamber and vitreous nearly to the baseline at PO 1 day after SC injection. The concentration of DSP in both anterior chamber and vitreous at PO 1 day after SC injection of DSP-NP was 5157±3952 ng/mL and 1286±851 ng/mL, respectively. High concentrations of DSP in both anterior chamber and vitreous was still detectable for DSP-NP at PO 7 day after SC administration, but the levels for SC administration of DSP were not detectable.

Hematogenic route, transscleral route and transcorneal route can contribute to the penetration of DSP into anterior chamber and even the vitreous after SC injection. Some may be due to the potential leakage of nanoparticles after the SC injection during the first 6 h. The aqueous solution of hydrophilic DSP could leak from the injection site as well, which reduces the retention time of injected DSP but increases DSP level at the tear film at the first several hours after SC injection, which could enhance the transcorneal route of drug delivery into the eye. The SC injection increased the exposure area of drug to the blood vessel, which enhanced the systemic update of drugs to blood circulation. Together with the leaked high DSP concentration at the precorneal surface, the blood DSP level for the SC injection of DSP was very high at the PO 2 h, which was more than 8-fold higher than the DSP-NP injection. DSP-NP showed better retention over the free DSP solution after the SC injection, and the DSP drug from DSP-NP was released at sustained manner.

In summary, constant levels of DSP have been achieved not only in intraocular tissues, but also in the blood for DSP-NP after the SC injection (constantly low level blood DSP level for SC injection of DSP-NP). The avoidance of high blood concentration may help to reduce the chance for systemic side effects of steroids.

About 20% of injected empty PLGA/F127 nanoparticles were retained in the conjunctiva tissues at PO day 7 and the gradual decrease of the fluorescence level from the nanoparticles may come from the degradation of nanoparticles and the cleavage of fluorescence dye from PLGA in the nanoparticle. The first big drop from 100% to 60% could mainly result from the leakage of the injected nanoparticles, however, this drop did not affect the desired constantly high levels of DSP in ocular tissues. Through careful administration and reduced injection volume, the leakage of nanoparticles from the SC injection can be minimized. A similar gradual decrease of the DSP levels at the extraocular tissue after the dissection of cornea, aqueous, vitreous and retina was also observed. It can result from the sustained release of DSP from the nanoparticles after the retention of DSP-NP in the conjunctiva tissues.

DSP was detected only in the as represented by the transcorneal DSP, not the physical absorbed DSP from aqueous humor and tear film. Cornea is a tight tissue comprising with epithelium, stroma and endothelium layer. Only drugs with suitable low molecular weight and hydrophilicity are able to penetrate the cornea. DSP is not suitable for the transcorneal penetration. Therefore, only at the very first hours, can one detect low level of DSP within cornea tissue when the DSP concentration at the tear film is extremely high. Routes other than the transcorneal penetration may contribute to the high level of DSP in intraocular tissue after SC injection.

The penetration of DSP into retina is negligible. It is well known that glucocorticoids can effectively inhibit the expression and action of most cytokines, and have been shown to induce T-cell apoptosis. Long-term glucocorticoid eye drops are required to prevent the cornea rejection after the normal PK. Long-term use of glucocorticoid eye drops can create safety issues and be a challenge to patient compliance. The studies described herein show that the once-a-week DSP-NP formulation for the SC injection is effective to achieve effective prevention of corneal allograft rejection. The high efficacy observed for the local treatment with the SC injection of DSP-NP was consistent with the high levels of DSP found in the AC humor. Compared with the control, DSP and PLGA/F127 NP groups, the DSP-NP treated group 1 lacked inflammatory cells in the histological studies. Inflammatory cells can produce various cytokines, including IL-2, TNF-a, VEGF. IL-2, TNF-a can increase major histocompatibility complex II antigen expression, activate macrophages and T lymphocytes leading to more cytokine release and cause immune rejection. The sustained release of high level DSP from DSP-NP after SC injection contributed to the great inhibition of inflammation and retardation of new vessel growth into the cornea relative to the control groups. The avascular nature of the cornea is crucial for maintaining its immunoprivilaged status at cornea transplantation, and neovascularization was believed to be a driving force for corneal rejection. SC injection of DSP had some effect at inhibiting of neovascularization of the corneal allografts, but the DSP level from the SC injection of DSP at once a week frequency is not enough to completely suppress the growth of new vessels. Even though dexamethasone shows higher anti-inflammatory potency (7:1 in comparison to prednisone), the shorter retention of high DSP levels after SC injection still greatly compromised its therapeutic efficacy.

Intraocular pressure increase was not observed during the whole 9 week study for the SC injection of DSP-NP. The majority of the encapsulated DSP, about 80%, was released at the first week of the in vitro release study, and remaining DSP at 1 week after injection dropped to approximately 5%. Therefore, if any side effects are observed or IOP increase, the DSP can be easily stopped through no further SC administration of DSP-NP. In comparison to other depot devices, no further surgery is required to remove the drug delivery devices. A one-week interval was effective in decreasing neovascularization and keeping the graft cornea clear. This interval may need to be lengthened to make this a clinically feasible treatment option, e.g. one month.

Biodegradable PLGA/F127 nanoparticles loaded with water-soluble glucocorticoid dexamethasone sodium phosphate (DSP-NP) were successfully constructed, and DSP-NP can release the DSP in a sustained manner up to 7 days. A prolonged retention of nanoparticles at the conjunctiva tissues was achieved through the SC injection at rats and constantly high DSP levels at ocular tissues were measured. The SC injection of DSP-NP effectively prevented corneal allograft rejection through the whole 9-week study, however, the control groups with free DSP resulted in graft failure in only 4 weeks. This strategy decreased the administration frequency, avoided the potential systemic side effects of glucocorticoids, which could potentially improve the patient compliance.

Example 2: Prevention of Neovascularization with DSP-NP

The biodegradable nanoparticle formulation that can provide sustained release of corticosteroid dexamethasone sodium phosphate (DSP) both in vitro and following SC injection in rats, demonstrated to prevent corneal allograft rejection in rats, was also shown to provide effective inhibition of corneal neovascularization.

Materials and Methods
Materials
Poly(D,L-lactic-co-glycolic acid; 50:50, Mw ~3.4 kDa, acid terminated) (PLGA) was purchased from Lakeshore Biomaterials (Evonik, Birmingham, Ala.). Dexamethasone sodium phosphate salt (DSP) was purchased from MP Biomedicals (Santa Ana, Calif.). [$^3$H]-labeled DSP was purchased from American Radiolabeled Chemicals (St Louis, Mo.). Pluronic F127 (a polyethylene oxide-polypropylene oxide-polyethylene oxide triblock copolymer, or PEO-PPO-PEO), triethanolamine (TEOA), ethylenediaminetetraacetic acid (EDTA) solution (0.5M), Zinc acetate dihydrate and all other organic solvents were purchased from Sigma-Aldrich (St. Louis, Mo.). Alexa Fluor 647 (AF647) cadaverine was purchased from Invitrogen (Carlsbad, Calif.).

Preparation of Fluorescently Labelled DSP-NP

Alexa Fluor 647 (AF647) cadaverine as a fluorescent marker, was chemically conjugated to PLGA using a method described by Xu, et al, J. Control. Release 170 (2013) 279-286. Nanoparticles composed of AF647-PLGA were prepared by a solvent diffusion (or nanoprecipitation) method. Briefly, a DSP-zinc complex was formed by adding 1 mL of 0.5 M zinc acetate aqueous solution to 0.5 mL of an aqueous solution containing 10 mg of DSP. After centrifugation at 10,000 g for 5 min, the precipitated complex and 50 mg PLGA (AF647-PLGA: PLGA at 1:3 w/w) were suspended and dissolved in 1.25 mL of THF followed by the addition of 20 μL of TEOA. The mixture was added dropwise into 100 mL of 5% F127 aqueous solution with stirring to form DSP-loaded PLGA nanoparticles (DSP-NP). After complete removal of the THF by solvent evaporation, 1 mL of 0.5 M EDTA aqueous solution (pH 7.5) was added to the nanoparticle suspension to chelate excess zinc and solubilize any unencapsulated DSP-zinc complexes. The fluorescently labelled DSP-NP were collected by centrifugation at 8,000 g for 25 min, washed with 5% F127, and resuspended in 0.2 mL of ultrapure water. The DSP-NP without the fluorescent label were prepared in similar method using PLGA only. Particle size and ζ-potential were determined by dynamic light scattering and laser Doppler anemometry, using a Zetasizer Nano ZS90 (Malvern Instruments, Southborough, Mass.). Samples were diluted in 10 mM NaCl solution at pH 7.2.

Retention of DSP-NP Following Subconjunctival Administration

The retention of DSP-NP after SC administration was investigated by imaging the whole eye with the Xenogen IVIS Spectrum optical imaging system (Caliper Life Sciences Inc., Hopkinton, Mass.). Rats were anesthetized by intramuscular injection of a mixture of Ketamine (80 mg/kg) and Xylazine (8 mg/kg). AF647 fluorescently labelled DSP-NP, were injected to Sprague Dawley rats by SC administration (50 μL) using a 27-gauge needle. The injection procedure was performed under an S81 operating ophthalmic microscope (Zeiss, Germany). The eye lids were retracted during imaging with a 45 G speculum (Focus Ophthalmics, LLC, Ontario, Calif.). The total fluorescence counts at the injection site were recorded at 640/680 nm. The images were analyzed using the Living Image 3.0 software (Caliper Lifesciences, Inc.), and the retention of nanoparticles was quantified by comparing to the fluorescence counts of the same eye immediately after injection of particles. Rat eyes without particle injection were used as the baseline.

In Vivo Ocular DSP Levels

Example 1 describes the in vivo ocular DSP level within 1 week after SC injection. The same method was used to detect the ocular DSP level after SC administration in rats at POD14. [$^3$H]-labeled DSP was blended with non-labeled DSP (10 μCi:1 mg DSP) and used in the preparation of DSP-NP. Fifty μL (~0.8 per eye) of the same formulation was administered to both eyes of the same animal (Sprague Dawley rat) through SC injection. At POD14, the rats under anesthesia were sacrificed after collecting two drops of blood from the tail vein. The aqueous, vitreous, and the remaining ocular tissues containing injection sites were carefully dissected and collected. All the samples were weighed and then dissolved with 2 mL of Solvable (Perkin Elmer, Waltham, Mass.) by incubation at 50° C. overnight. Blood samples were bleached with 0.2 mL $H_2O_2$ and 20 μL 0.5M EDTA. Ten milliliters of Ultima gold scintillation medium (Perkin Elmer, Waltham, Mass.) was added before counting the radioactivity in a scintillation counter (Perkin Elmer, Waltham, Mass.). The results were expressed as a percentage of the injected dose and are the mean±standard deviation (SD) of four eyes per data point. The level of DSP in blood was the average of two animals per time point. The total percentage of the injected dose at the injection sites and the radioactivity per mg of tissue or mL of blood were calculated.

Animals

All experimental protocols were approved by the Johns Hopkins Animal Care and Use Committee. 6-8 weeks old male Sprague Dawley rats (weighing 200-250 g) were purchased from Harlan (Indianapolis, Ind.). All rats were cared for and treated in accordance with the Association for Research in Vision and Ophthalmology (ARVO) resolution concerning the use of animals in ophthalmological research. The animals were anesthetized with intramuscular injection of a mixture of Ketamine (80 mg/kg) and Xylazine (8 mg/kg) during experimental procedures. The topical anesthesia was achieved with instillation of 0.5% proparacaine eye drops on the eyes.

Corneal NV Model by Suturing

Corneal NV model was induced by placing sutures in the cornea. Briefly, rats were anesthetized with an intramuscular injection of a mixture of Ketamine (80 mg/kg) and Xylazine (8 mg/kg). Repeated instillations of 0.5% tropicamide eye drops and 0.5% proparacaine were used for total pupil dilation and topical anesthesia before surgery, respectively. Corneal NV was induced by placing two suture stitches in the superior cornea with 10-0 nylon (Alcon Laboratories, Inc, Fort Worth, Tex.) under an operating microscope. The distance between the stitches and the limbus was approximately 2 mm and there was a distance of 1 mm between the two stitches. After the placement of sutures, animals were immediately administered with subconjunctival injection of: a) 50 µL DSP-NPs at a concentration of 6 mg DSP/mL, b) 50 µL DSP solution (6 mg DSP/mL) and c) saline control. Erythromycin antibiotic ointment was applied to the cornea to prevent corneal inflammation and cornea dry-up.

Corneal NV Quantification

Corneal NV was observed by both digital camera and slit-lamp microscopy (SL120; Carl Zeiss AG, Oberkochen, Germany). Rats were anesthetized with an intramuscular injection of a mixture of Ketamine (80 mg/kg) and Xylazine (8 mg/kg). Repeated instillations of 0.5% tropicamide eye drops were used to fully dilate the pupils before imaging. Slit lamp photographs were taken at 12× magnification. Slit-lamp photographs of corneas were used to quantify the corneal neovascularization using Adobe Photoshop CS5 (Adobe Corp., San Jose, Calif., USA). The arc along the limbus for the vascularized area was drawn and vascularized area pixel was measured. Corneal NV area was calculated using vascularized area pixel/1 $mm^2$ area pixel. The vascularized area was divided into six sections; distances between vessel tips and the limbus at the five intersection points of the arc were measured as vessel lengths, and the average vessel length was calculated as the final new vessel length of each cornea. All parameters were measured by an investigator who was blind of the treatment assignment.

Intraocular Pressure Measurement

Non-invasive intraocular pressure (IOP) measurements were conducted weekly after the surgery using an Icare® Tonolab (Helsinki, Finland). The IOP recorded for each eye was the average of three consecutive measurements±standard error of the mean (SEM).

Cornea Histopathology Study

At 7 days and 14 days post-operation, all animals were sacrificed, and the eyes that underwent the suture procedure were enucleated. Eye tissues were fixed with 10% formalin for 24 hours before being embedded in paraffin. Axial sections (5 µm thick) with antero-posterior orientation (from the cornea to the optic nerve) were cut, and stained with H&E.

Real-Time Quantitative Reverse Transcription Polymerase Chain Reaction (RT-PCR)

The mRNA expression levels of some angiogenesis cytokines including VEGF, MMP-2, MMP-9, basic fibroblast growth factor (bFGF), TNF-alpha in the corneas were measured using RT-PCR. Corneas were dissected from the treated eyes at 7 and 14 days post-operation, respectively, and pooled together (n=3). Total ribonucleic acid (RNA) was isolated with TRIzol® reagent (Invitrogen, Grand Island, N.Y., USA), according to the manufacturer's instructions. Then RNA was transcribed into complementary DNA using the High Capacity cDNA Reverse Transcription Kit (No. 4368814, Applied Biosystems, Foster City, Calif., USA), according to the manufacturer's instructions. RT-PCR was carried out using a 7100 RealTime PCR System (Applied Biosystems, Foster City, Calif.) with Fast SYBR® Green Master Mix (Applied Biosystems, Foster City, Calif.). The primers used were listed in Table 2. All expression levels were normalized to GAPDH and compared with each other. The results were presented as the average of three repeats±standard error of the mean (SEM).

TABLE 2

RT-PCR primers sequences

| | Primer sequence | Product size | Sequence ID NO. |
|---|---|---|---|
| VEGF | Forward: GCCCATGAAGTGGTGAAGTT | 172 bp | SEQ ID NO: 1 |
| | Reverse: ACTCCAGGGCTTCATCATTG | | SEQ ID NO: 2 |
| MMP-2 | Forward: AGCTTTGATGGCCCCTATCT | 150 bp | SEQ ID NO: 3 |
| | Reverse: GGAGTGACAGGTCCCAGTGT | | SEQ ID NO: 4 |
| MMP-9 | Forward: CCACCGAGCTATCCACTCAT | 159 bp | SEQ ID NO: 5 |
| | Reverse: GTCCGGTTTCAGCATGTTTT | | SEQ ID NO: 6 |
| bFGF | Forward: GAACCGGTACCTGGCTATGA | 182 bp | SEQ ID NO: 7 |
| | Reverse: CCGTTTTGGATCCGAGTTTA | | SEQ ID NO: 8 |
| TNF-α | Forward: ACTCCCAGAAAAGCAAGCAA | 211 bp | SEQ ID NO: 9 |
| | Reverse: CGAGCAGGAATGAGAAGAGG | | SEQ ID NO: 10 |

TABLE 2-continued

RT-PCR primers sequences

| | Primer sequence | Product size | Sequence ID NO. |
|---|---|---|---|
| GAPDH | Forward: TGCCACTCAGAAGACTGTGG<br>Reverse: TGGGGGTAGGAACACAGAAG | 170 bp | SEQ ID NO: 11<br>SEQ ID NO: 12 |

Statistical Analysis

All data collected were compared among groups using t test and multiple comparisons test (one-way ANOVA, Bonferroni test). Differences were considered to be statistically significant at a level of P<0.05.

Results

Characterization of DSP-NP In Vitro and In Vivo

Water soluble corticosteroid dexamethasone sodium phosphate (DSP) was successfully encapsulated into PLGA nanoparticles (DSP-NP) using the zinc chelator. In order to quantify the retention of biodegradable DSP-NP after subconjunctival administration, the PLGA was fluorescently labelled through conjugating AF-647 dye to PLGA before preparation of DSP-NP. The conjugation of AF-647 to PLGA did affect the physiochemical properties of DSP-NP with 8% drug loading and around 200 nm particle size (Table 3). After SC administration of AF-647-labelled DSP-NP, the live animal imaging was used to quantify the fluorescence signal in the eyes over 3 weeks retention study (FIG. 3). A rapid drop of the fluorescent signal down to 20% of the original signal was observed during the first 2 days.

TABLE 3

Physicochemical properties of nanoparticles

| Formulation | Diameter (nm) | PDI | ζ-potential (mV) | DL (%) |
|---|---|---|---|---|
| DSP-NP | 200 ± 8 | 0.12 | −8 ± 1.4 | 8 |
| AF647-DSP-NP | 186 ± 13 | 0.086 | −6 ± 1 | 8 |

Figure 10A:
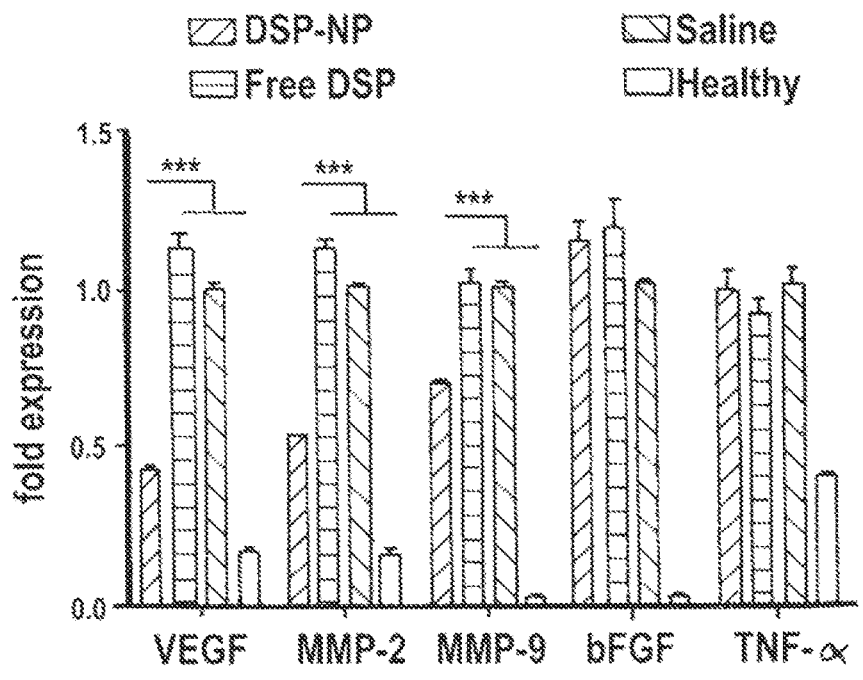
FIGS. 10A and 10B are graphs of the cytokine levels related to corneal neovascularization at (FIG. 10A) PO 7 days and (FIG. 10B) PO 14 days measured by RT-PCR for DSP-NP; free DSP; saline; and healthy.
Figure 10B:
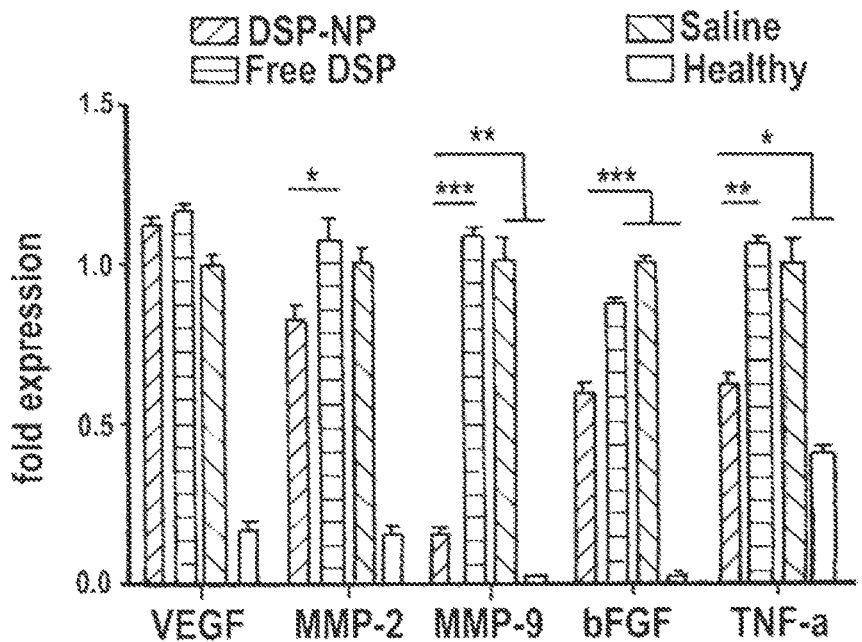
Figure 11:
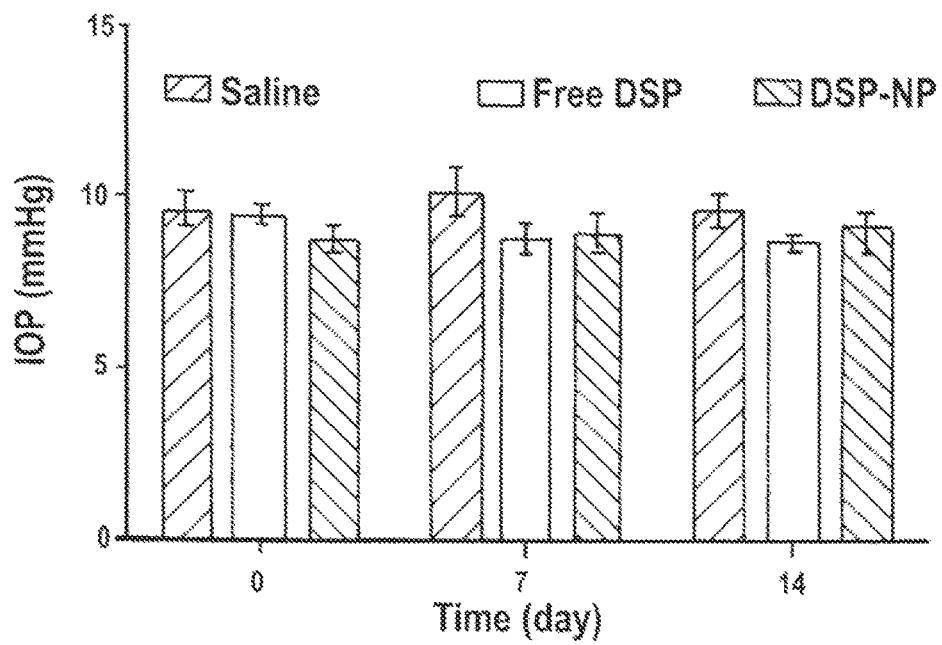
FIG. 11 is a graph of IOP (mm Hg) after treatment of SC injection of saline, free DSP and DSP-NP.

The levels of VEGF, MMP-2, MMP-9, bFGF, and TNF-α are shown in FIGS. 10A (at seven days) and 10B (at 14 days). The intraocular pressures are shown in FIG. 11.

Example 3: Prevention of Uveitis

Uveitis is a sight-threatening inflammatory ocular disease. Corticosteroids are the most effective treatment of uveitis. However, intermediate and posterior uveitis affects the vitreous and the retina, which is hard to treat with topical steroids. Water-soluble steroid solution injected subconjunctivally is eliminated very quickly, requiring repeated injections to maintain therapeutic levels for a long period time. Nanoparticles (NP) loaded with dexamethasone sodium phosphate (DSP) provide high drug loading and prolonged drug release. These were tested for efficacy in a rat panuveitis model.

Methods:

Biodegradable Poly (lactic-co-glycolic acid), (PLGA) nanoparticles containing DSP were prepared using a modified solvent diffusion method. endotoxicin-induced uveitis (EIU) model was initiated 24 hours testing using IP injection of liposaccharide (LPS) to 6 week old Lewis rats. The ability of DSP-loaded nanoparticles to reduce inflammation in rats immunized by LPS was tested by clinical evaluation, mRNA expression and protein level of inflammatory cytokines in retina and histopathology.

Figure 12:
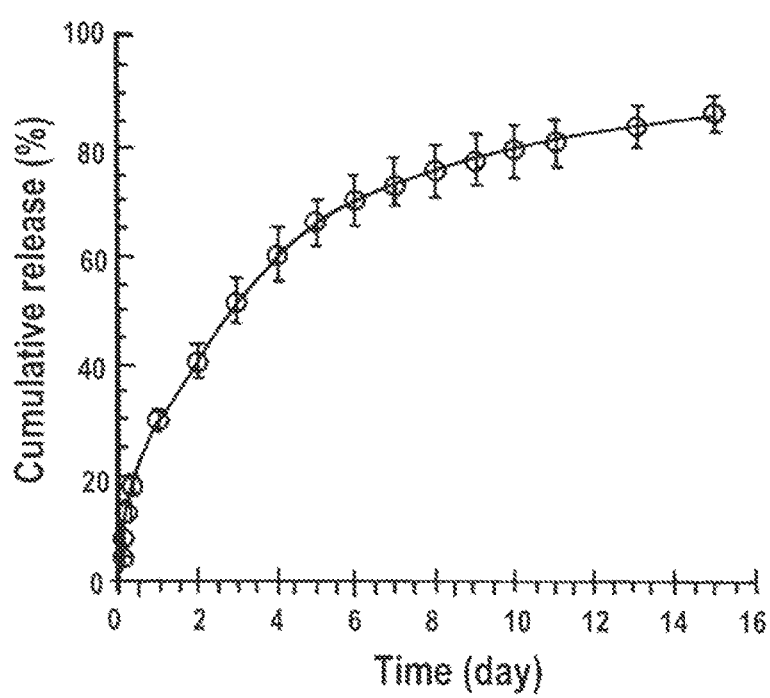
FIG. 12 is a graph of sustained drug release over 15 days in vitro under sink conditions of DSP-NP exhibited a size of 200±8 nm, 8 wt % drug loading.

Results:

Nanoparticles exhibited an average diameter of 200 nm, high drug loading of 8 wt % and controlled drug release profiles over 15 days. FIG. 12 is a graph of sustained drug release over 15 days in vitro under sink conditions of DSP-NP.

Figure 13A:
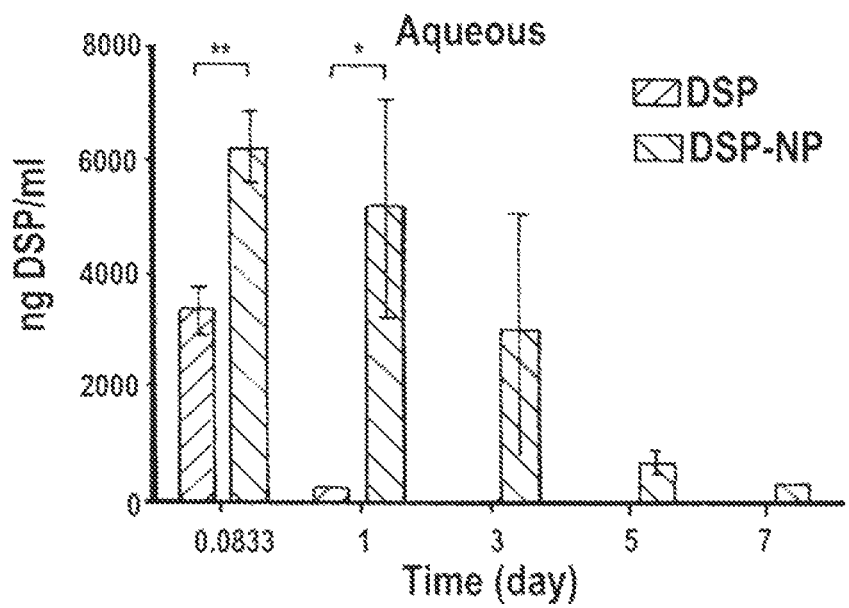
FIGS. 13A and 13B are graphs of sustained high ocular drug levels for at least 7 days after SC administration of DSP-NP in rats showing high drug levels in both anterior chamber (FIG. 13A) and vitreous (FIG. 13B).
Figure 13B:
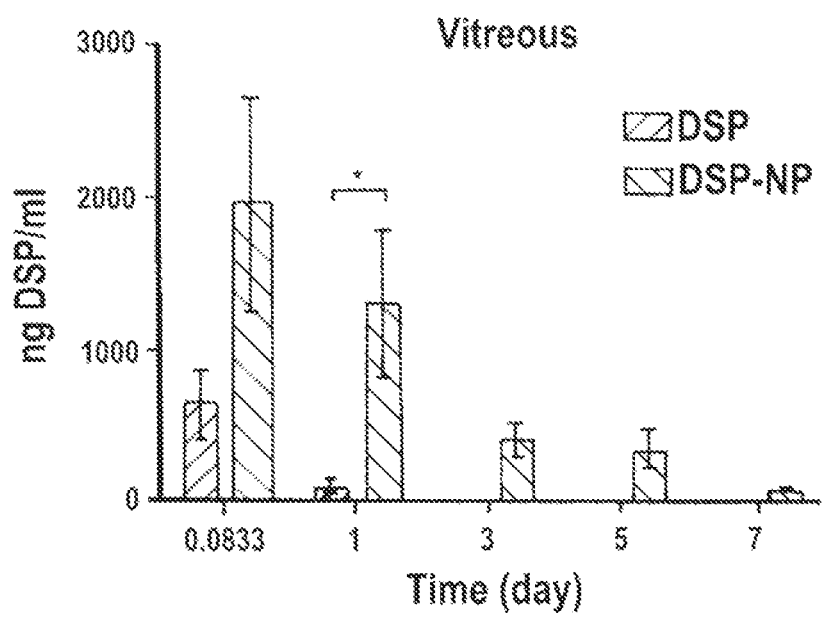

These DSP-loaded nanoparticles provided sustained ocular drug levels after subconjunctival administration to rat eyes. FIGS. 13A and 13B are graphs of sustained high ocular drug levels for at least 7 days after SC administration of DSP-NP in rats showing high drug levels in both anterior chamber (FIG. 13A) and vitreous (FIG. 13B).

Figure 14:
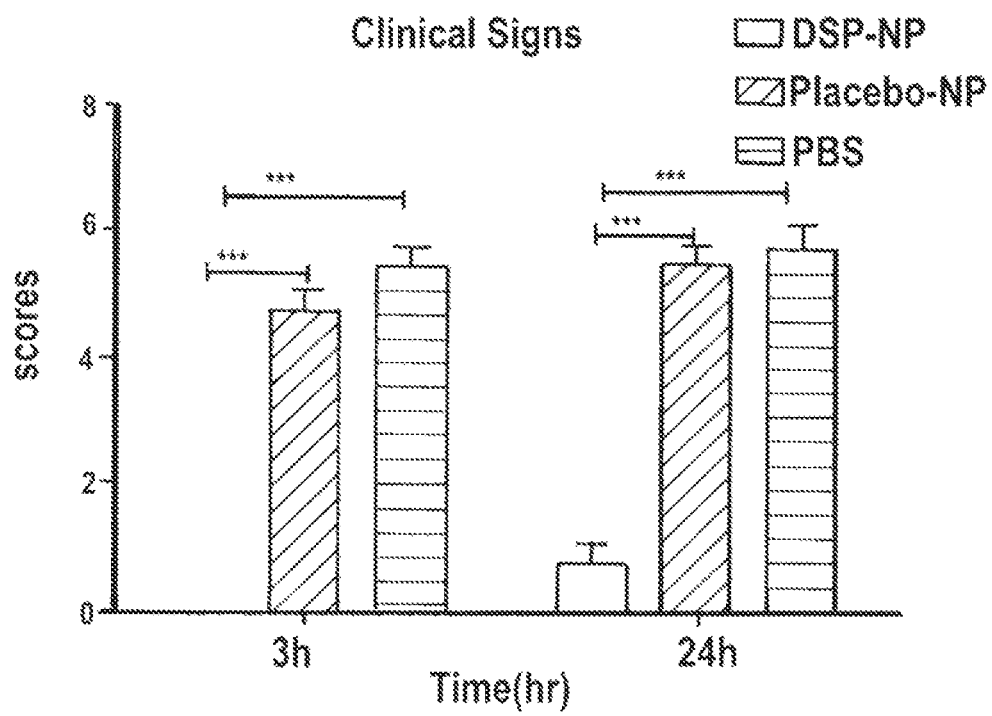
FIG. 14 is a graph of inflammation score of anterior segment imaged and scored at 3 hours and 24 hours after IP injection of LPS, showing DSP-NP prevention group has significantly less inflammation than control groups.
Figure 15:
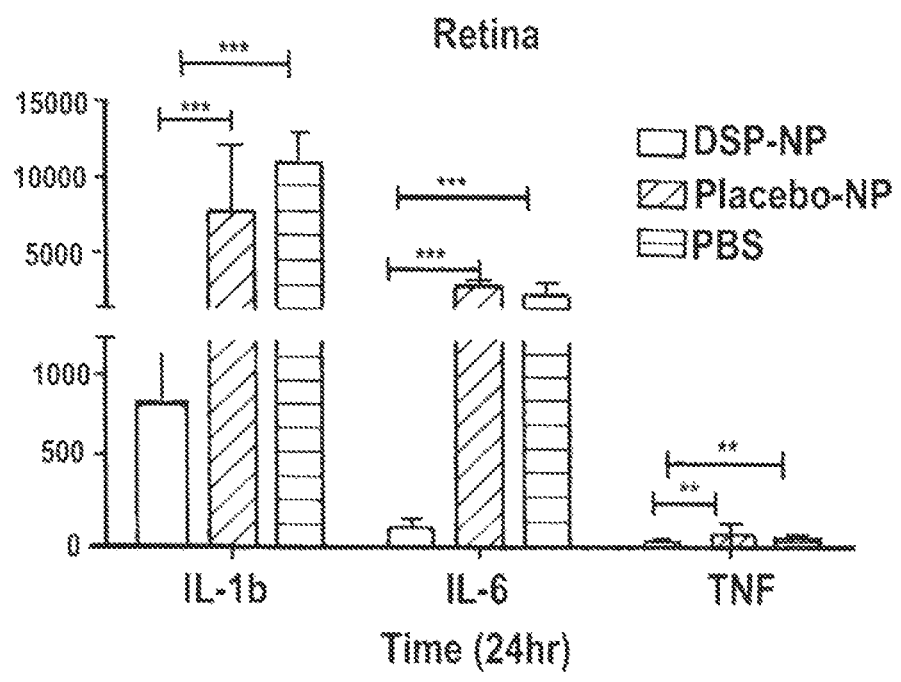
FIG. 15 is a graph of mRNA expression of IL-1b, IL-6 and TNF in retina in three groups of EIU model after 24 hour immunization, showing significantly decreased expression in DSP-NP group compared to placebo-NP and PBS groups.

Comparison to control treatment groups of placebo particles, saline or free drug solution, showed that DSP-loaded NP treatment of the uveitis rat model displayed significantly lower inflammation scores, mRNA expression and inflammatory cytokine protein levels. FIG. 14 is a graph of the inflammation scores of anterior segment imaged and scored at 3 hours and 24 hours after IP injection of LPS, showing DSP-NP prevention group has significantly less inflammation than control groups. FIG. 15 is a graph of mRNA expression of IL-1b, IL-6 and TNF in retina in three groups of EIU model after 24 hour immunization, showing significantly decreased expression in DSP-NP group compared to placebo-NP and PBS groups.

Conclusion:

PLGA nanoparticles loaded with dexamethasone sodium phosphate provide sustained release of corticosteroids and effectively decrease the inflammation associated with uveitis in rats. As uveitis often recurs, this treatment should reduce administration frequency, avoid potential systemic side effects of corticosteroids, and improve patient compliance, which has promising clinical application.

Example 4: Monthly Subconjunctival Administration of Corticosteroid Nanoparticles for Treating Corneal Allograft Rejection and Glaucoma in Rats Materials and Methods Nanoparticles were prepared using Polylactic acid with COOH groups for encapsulation of DSP, as described in Example 1.

The nanoparticles were administered to rats as described in Example 2 for prevention of corneal neovascularization using a monthly subconjunctival injection.

The nanoparticles were also administered to a model for glaucoma.

Results

The nanoparticles have a diameter of 338±11 nm; a PDI of 0.09±0.038, a ζ-potential (mV) 0f−3±1 and a DL % of 9.4±0.8.

Figure 16A:
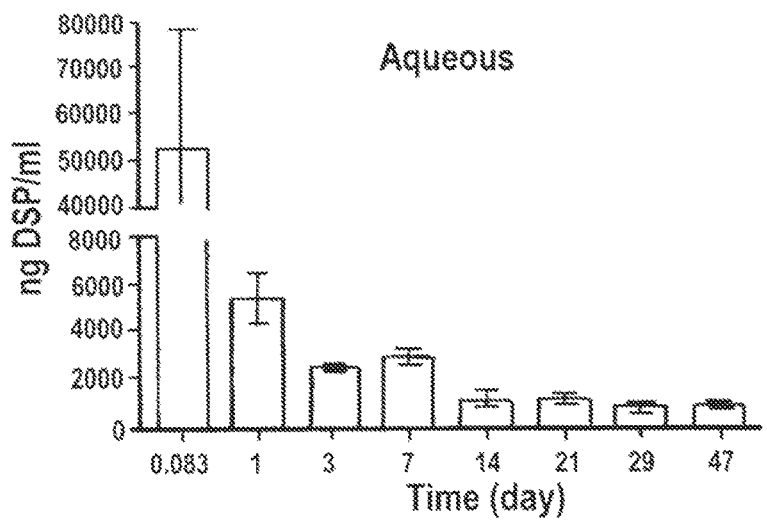
FIGS. 16A-16D are graphs of the pharmacokinetics (ng DSP/ml over time in days) of subconjunctival injection of DSP-PLA2COOH nanoparticles to rats.
Figure 16B:
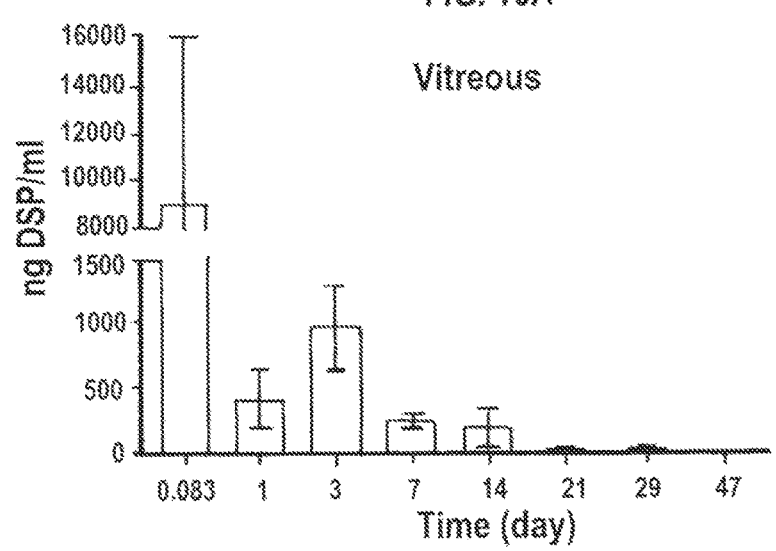
Figure 16C:
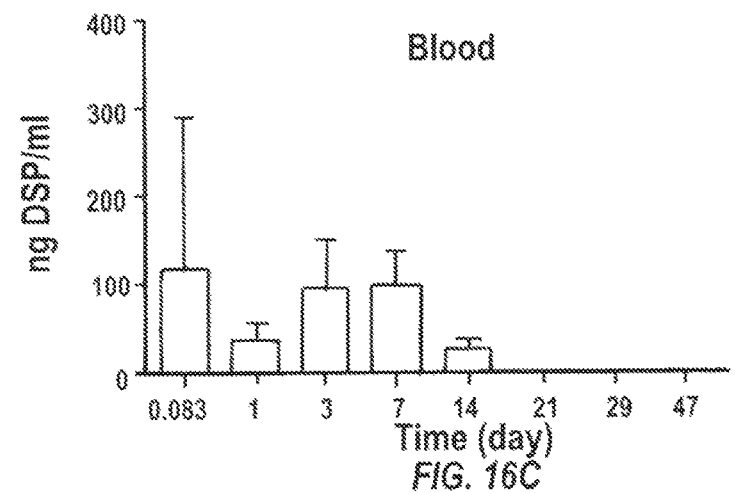
Figure 16D:
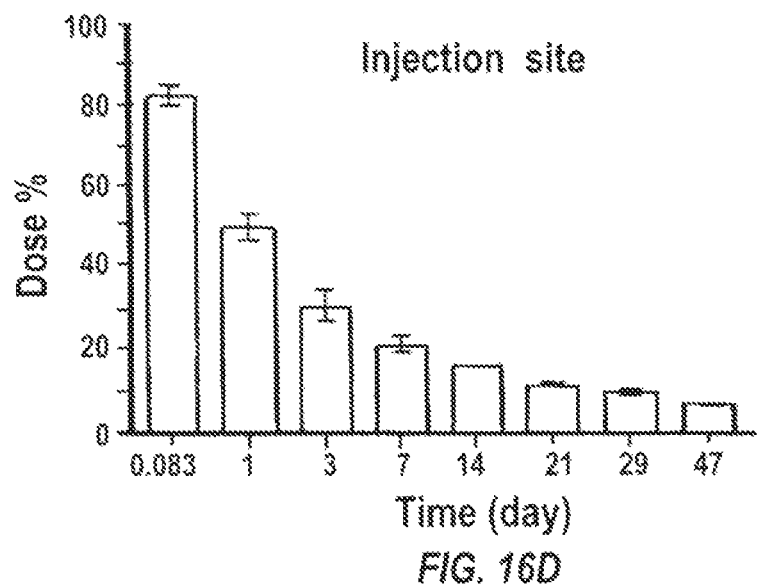

The results are shown in FIGS. 16A-16D for the pharmacokinetic study showing the DSP levels over time. FIGS. 16A-16D are graphs of the pharmacokinetics (ng DSP/ml over time in days) of subconjunctival injection of DSP-PLA2COOH nanoparticles to rats. FIG. 16A, aqueous; FIG. 16B, vitreous; FIG. 16C, blood; and FIG. 16D, injection site control.

Figure 17A:
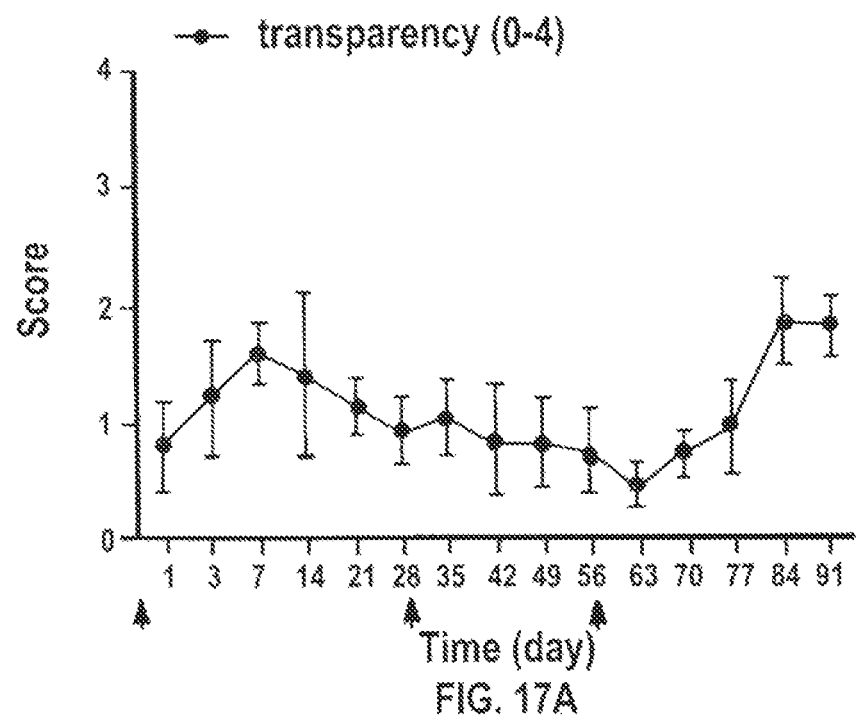
FIGS. 17A-17E are graphs of the clinical observation of the grafts over time in days during the whole 12 week follow up for (17A-17C) the DSP-PLA2COOH nanoparticles treated group and (17D-17F) the saline control group. Arrows indicate the treatment injection time points.
Figure 17B:
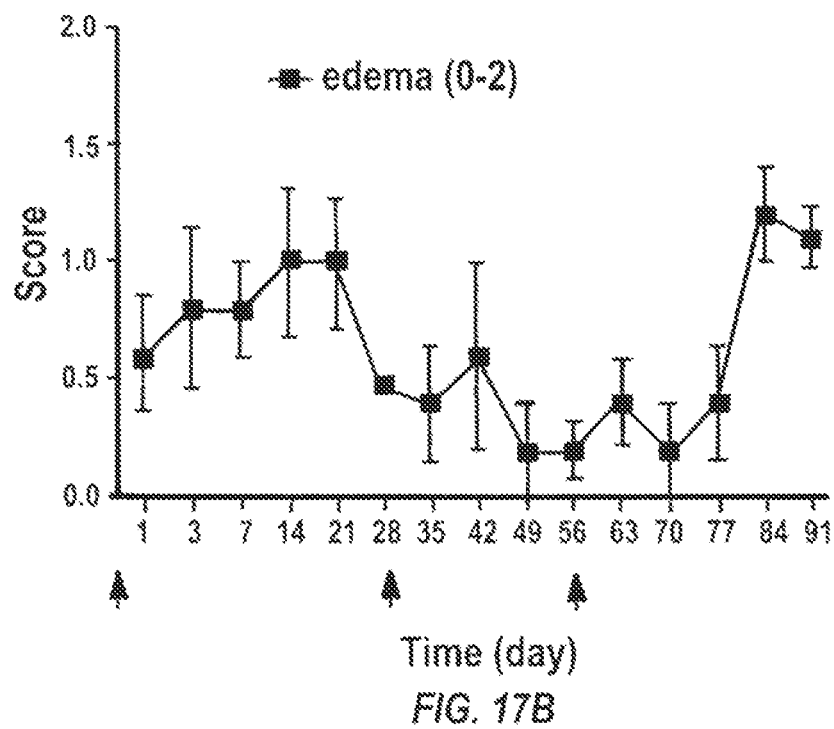
Figure 17C:
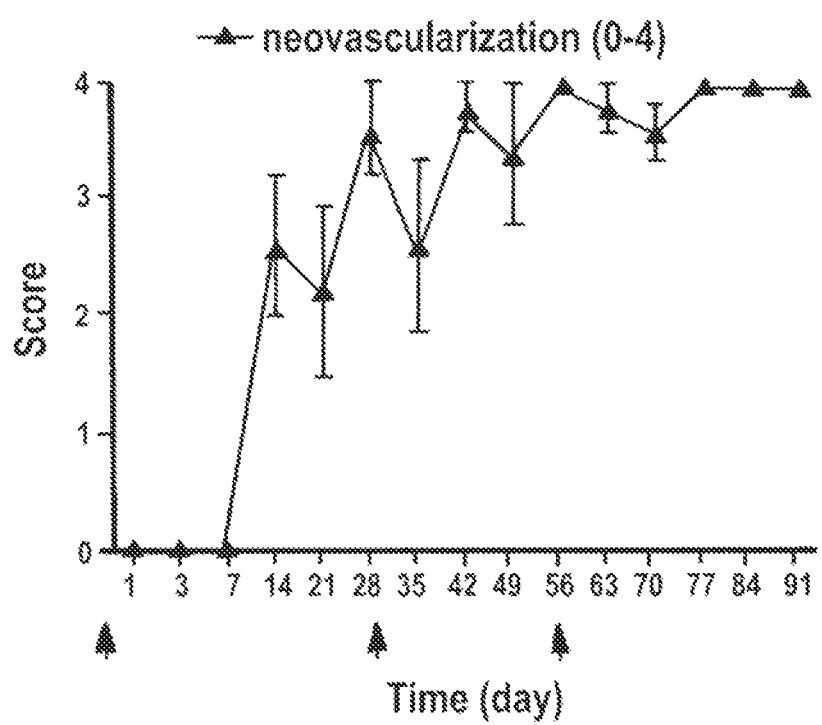
Figure 17D:
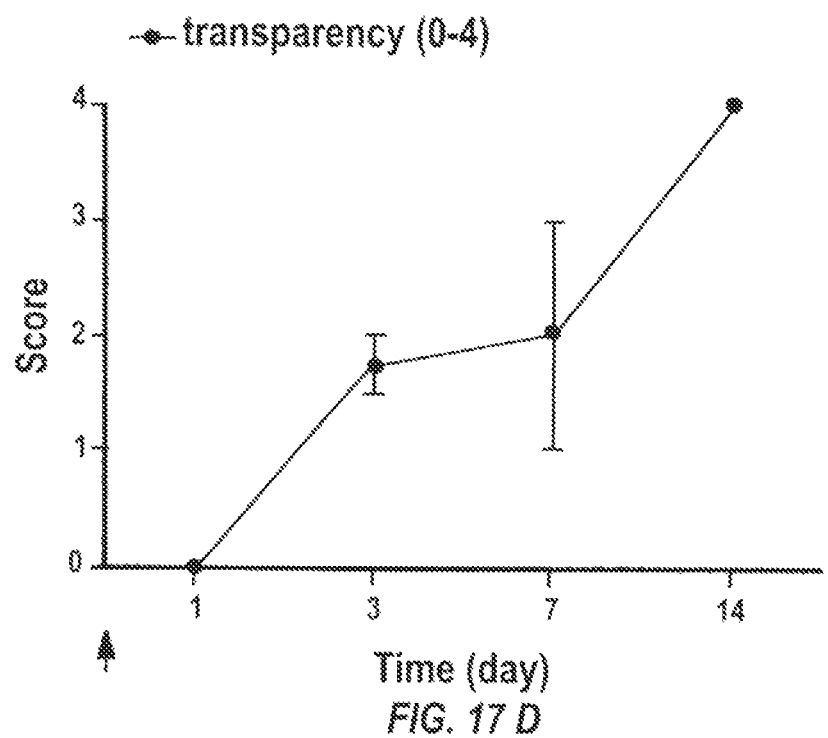
Figure 17E:
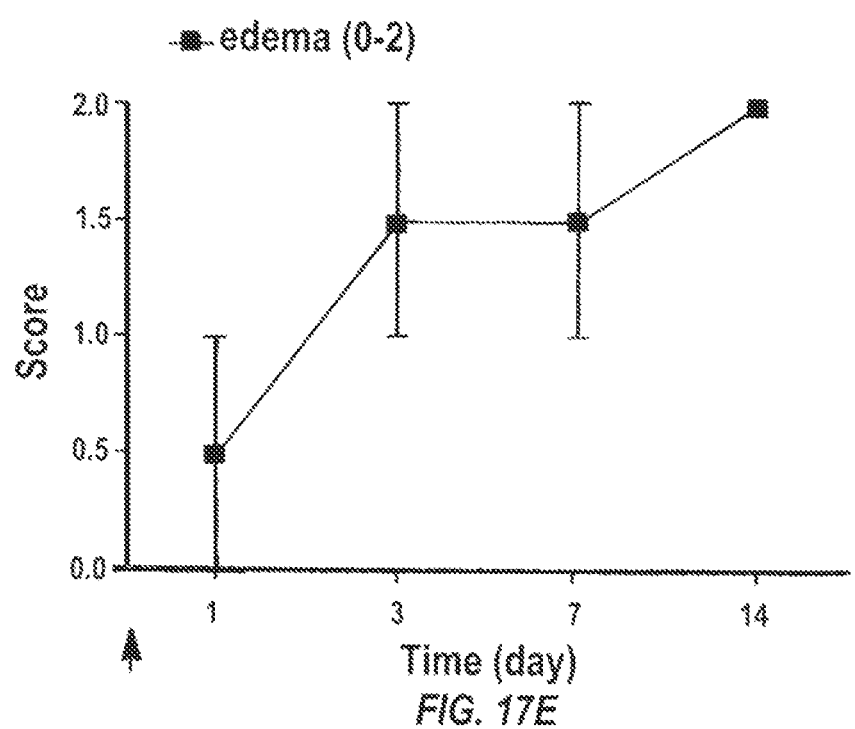
Figure 17F:
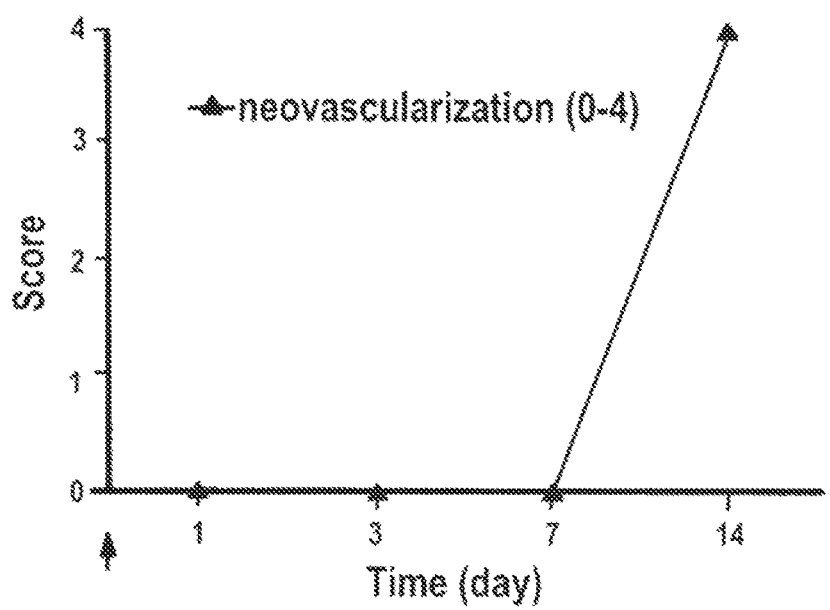

FIGS. 17A-17E are graphs of the clinical observation of the grafts over time in days during the whole 12 week follow up for (17A-17C) the DSP-PLA2COOH nanoparticles treated group and (17D-17F) the saline control group. Arrows indicate the treatment injection time points. FIGS. 17A, 17D are transparency score; FIGS. 17B, 17E are edema score, and 17C, 17F are neovascularization.

Figure 18:
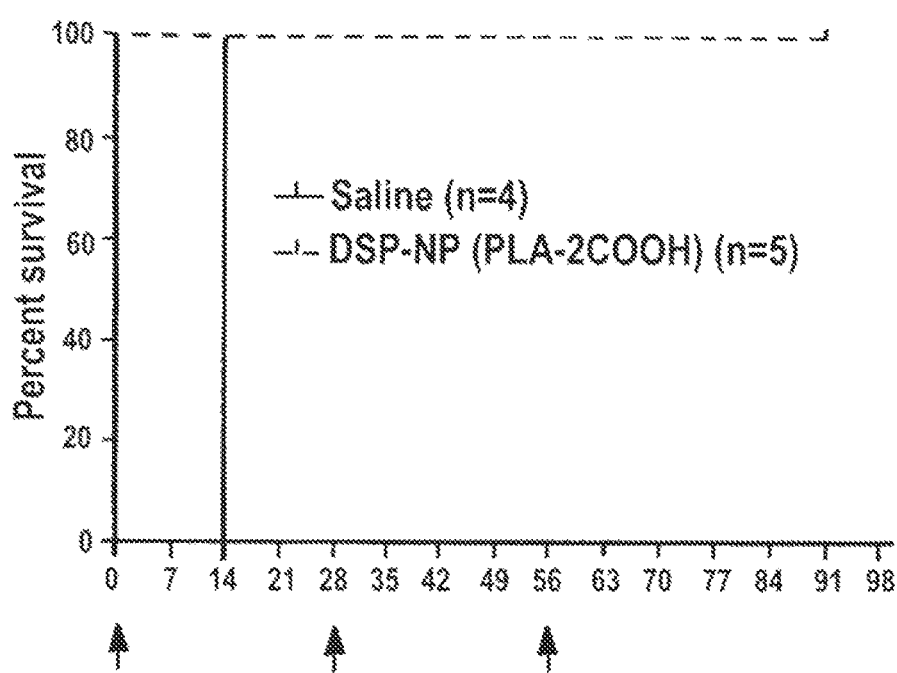
FIG. 18 is a survival curve (percent survival over time in days) for both the saline control group and the DSP-PLA2COOH nanoparticle treated group.

FIG. 18 is a survival curve (percent survival over time in days) for both the saline control group and the DSP-PLA2COOH nanoparticle treated group.

Figure 19A:
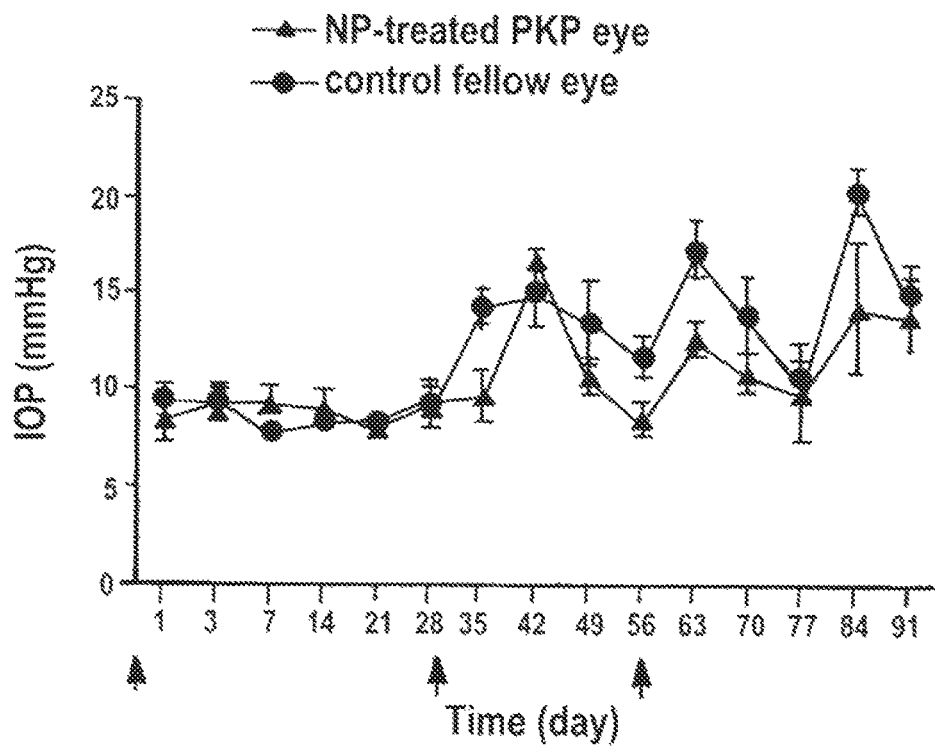
FIGS. 19A and 19B are graphs of intraocular pressure over time in days for animals treated with the DSP-PLA2COOH nanoparticles at monthly intervals (19A) as compared to control (19B).
Figure 19B:
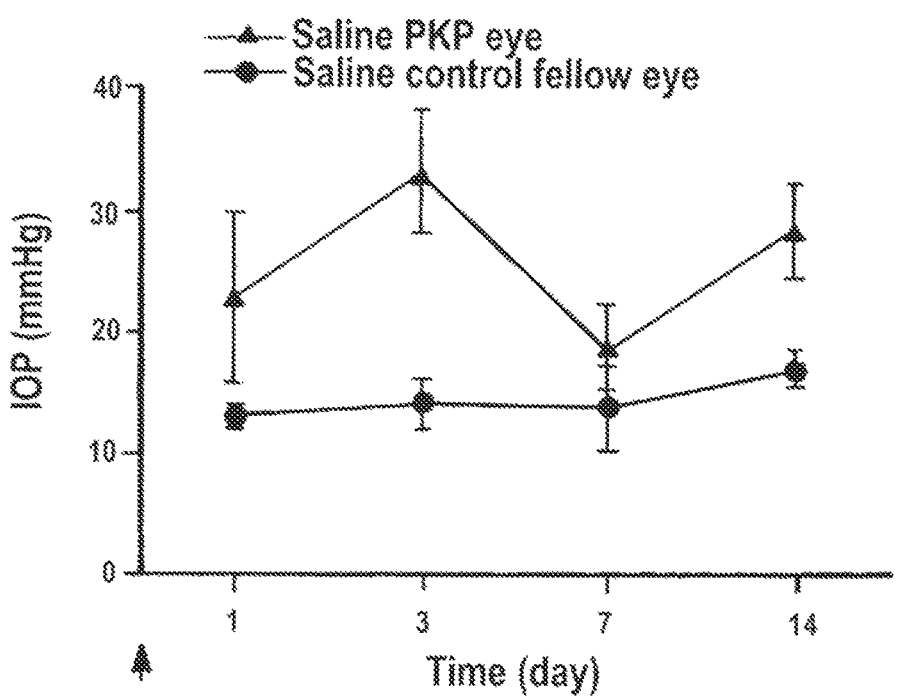

FIGS. 19A and 19B are graphs of intraocular pressure over time in days for animals treated with the DSP-PLA2COOH nanoparticles at monthly intervals (19A) as compared to control (19B).

The results demonstrate comparable results are obtained with a monthly injection for both prevention of graft rejection as well as treatment of glaucoma using the DSP-PLA2COOH nanoparticles.

We claim:

1. Biodegradable polymeric particles densely coated with hydrophilic polymer and encapsulating glucocorticoid complexed by chelation of metal ions via phosphate or carboxyl groups to the biodegradable polymer forming the particles,
    wherein the glucocorticoid is derivatized into a water soluble salt, and then incorporated into the polymer particles
    wherein the particles provide sustained release of the glucocorticoid for up to seven days in vitro,
    wherein the particles can be administered through subconjunctival (SC) injection, and
    wherein the particles are retained in the conjunctiva tissue of the eye for two weeks.

2. The particles of claim 1 wherein the glucocorticoid is dexamethasone sodium phosphate (DSP).

3. The particles of claim 1 wherein the biodegradable polymer is selected from the group consisting of polyhydroxy acids, polyhydroxyalkanoates, polyanhydrides and carboxyl group-terminated polymers thereof.

4. The particles of claim 1 comprising nanoparticles having an average diameter between 100 nanometers and up to one micron.

5. The particles of claim 1 comprising poly(lactic-co-glycolic acid) (PLGA) which is densely coated with polyethylene glycol (PEG), polyoxyethylene-polyethylene oxide block copolymers or combinations thereof.

6. The particles of claim 1 wherein the glucocorticoid is complexed by chelation of metal ions with phosphate or carboxyl groups to the biodegradable polymer prior to or at the time of forming the particles.

7. The particles of claim 1 wherein the glucocorticoid is complexed to carboxyl end groups at the terminus of the biodegradable polymer forming the particles via an ester or other hydrolysable moiety.

8. The particles of claim 1 in a pharmaceutically acceptable excipient for administration to the eye.

9. A method for preventing inflammation, graft rejection, or neovascularization comprising administering an effective amount of the particles of claim 1 to the eye or tissues adjacent to the eye.

10. The method of claim 9 wherein the particles are administered locally to the eye by front, mid or back vitreal injection, subconjunctival injection, intracameral injection, injection into the anterior chamber via the temporal limbus, intrastromal injection, injection into the subchoroidal space, intracorneal injection, subretinal injection, or intraocular injection.

11. The method of claim 9 wherein the particles are administered by intravitreal injection to prevent or decrease vascularization.

12. The method of claim 9 wherein the particles are administered by subconjunctival (SC) injection and retained in the conjunctiva tissue.

13. The method of claim 9 wherein the particles are administered to prevent or decrease neovascularization.

14. The method of claim 9 wherein the particles are administered to prevent graft rejection.

15. The method of claim 9 wherein the particles are administered no less frequently than once a week, once every two weeks, once every four weeks, once a month, once every two months, or once every three months.

16. The method of claim 9 wherein the particles are nanoparticles less than one micron in diameter.

17. The method of claim 9 wherein the particles are microparticles up to 100 microns in diameter.

18. The particles of claim 1 wherein the glucocorticoid is complexed by chelation of metal ions to carboxyl end groups at the terminus of the polymer forming the particles.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
gcccatgaag tggtgaagtt                                                 20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
actccagggc ttcatcattg                                                 20

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
agctttgatg gcccctatct                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
ggagtgacag gtcccagtgt                                                 20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
ccaccgagct atccactcat                                                 20

<210> SEQ ID NO 6
```

-continued

```
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
gtccggtttc agcatgtttt                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
gaaccggtac ctggctatga                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
ccgttttgga tccgagttta                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
actcccagaa aagcaagcaa                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
cgagcaggaa tgagaagagg                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
tgccactcag aagactgtgg                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
```
tgggggtagg aacacagaag                                               20